US007968749B2

(12) United States Patent
Frenkel et al.

(10) Patent No.: US 7,968,749 B2
(45) Date of Patent: Jun. 28, 2011

(54) PROCESS FOR PREPARING AND DRYING SOLID RASAGILINE BASE

(75) Inventors: Anton Frenkel, Netanya (IL); Ronen Ben-David, Netanya (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 12/456,643

(22) Filed: Jun. 19, 2009

(65) Prior Publication Data

US 2009/0318564 A1    Dec. 24, 2009

Related U.S. Application Data

(60) Provisional application No. 61/132,487, filed on Jun. 19, 2008.

(51) Int. Cl.
C07C 211/42    (2006.01)
A61K 31/135    (2006.01)

(52) U.S. Cl. ........................................ 564/308; 514/647
(58) Field of Classification Search ........................ None
See application file for complete search history.

(56) References Cited

U.S. PATENT DOCUMENTS

| | | | |
|---|---|---|---|
| 5,387,612 | A | 2/1995 | Youdim et al. |
| 5,453,446 | A | 9/1995 | Youdim et al. |
| 5,457,133 | A | 10/1995 | Youdim et al. |
| 5,486,541 | A | 1/1996 | Sterling et al. |
| 5,519,061 | A | 5/1996 | Youdim et al. |
| 5,532,415 | A | 7/1996 | Youdim et al. |
| 5,576,353 | A | 11/1996 | Youdim et al. |
| 5,599,991 | A | 2/1997 | Youdim et al. |
| 5,668,181 | A | 9/1997 | Youdim et al. |
| 5,744,500 | A | 4/1998 | Youdim et al. |
| 5,786,390 | A | 7/1998 | Youdim et al. |
| 5,891,923 | A | 4/1999 | Youdim et al. |
| 6,126,968 | A | 10/2000 | Peskin et al. |
| 6,277,886 | B1 | 8/2001 | Levy et al. |
| 6,316,504 | B1 | 11/2001 | Youdim et al. |
| 6,462,222 | B1 | 10/2002 | Chorev et al. |
| 6,630,514 | B2 | 10/2003 | Youdim et al. |
| 6,956,060 | B2 | 10/2005 | Youdim et al. |
| 7,396,860 | B2 | 7/2008 | Blaugrund et al. |
| 7,491,847 | B2 | 2/2009 | Frenkel |
| 7,547,806 | B2 | 6/2009 | Frenkel et al. |
| 7,572,834 | B1 | 8/2009 | Sterling et al. |
| 7,598,420 | B1 | 10/2009 | Sterling et al. |
| 7,619,117 | B1 | 11/2009 | Lidor-Hadas et al. |
| 7,750,051 | B2 | 7/2010 | Frenkel et al. |
| 7,815,942 | B2 | 10/2010 | Peskin |
| 7,855,233 | B2 | 12/2010 | Frenkel et al. |
| 2006/0018957 | A1 | 1/2006 | Lerner et al. |
| 2006/0094783 | A1 | 5/2006 | Youdim et al. |
| 2006/0188581 | A1 | 8/2006 | Peskin |
| 2007/0100001 | A1 | 5/2007 | Youdim et al. |
| 2007/0112217 | A1 | 5/2007 | Frenkel |
| 2007/0232700 | A1 | 10/2007 | Blaugrund et al. |
| 2008/0161408 | A1 | 7/2008 | Frenkel et al. |
| 2009/0062400 | A1 | 3/2009 | Oron et al. |
| 2009/0076160 | A1 | 3/2009 | Lendvai et al. |
| 2009/0111892 | A1 | 4/2009 | Patashnick et al. |
| 2009/0181086 | A1 | 7/2009 | Safadi et al. |
| 2009/0312436 | A1 | 12/2009 | Levy et al. |
| 2010/0008983 | A1 | 1/2010 | Safadi et al. |
| 2010/0010095 | A1 | 1/2010 | Frenkel |
| 2010/0010098 | A1 | 1/2010 | Elffrink |
| 2010/0029987 | A1 | 2/2010 | Allegrini et al. |
| 2010/0137447 | A1 | 6/2010 | Lehmann et al. |
| 2010/0144887 | A1 | 6/2010 | Frenkel et al. |
| 2010/0145101 | A1 | 6/2010 | Frenkel et al. |
| 2010/0168239 | A1 | 7/2010 | Poewe |
| 2010/0189787 | A1 | 7/2010 | Safadi et al. |
| 2010/0189788 | A1 | 7/2010 | Safadi et al. |
| 2010/0189790 | A1 | 7/2010 | Safadi et al. |
| 2010/0189791 | A1 | 7/2010 | Frenkel et al. |
| 2010/0190859 | A1 | 7/2010 | Frenkel et al. |
| 2010/0234636 | A1 | 9/2010 | Stahl |

FOREIGN PATENT DOCUMENTS

| | | |
|---|---|---|
| WO | WO 2007/101400 | 9/2007 |
| WO | WO 2008/131961 | 11/2008 |
| WO | WO 2009/081148 | 7/2009 |
| WO | WO 2009/122301 | 10/2009 |
| WO | WO 2009/152777 | 12/2009 |
| WO | WO 2010/007181 | 1/2010 |
| WO | WO 2010/013048 | 2/2010 |
| WO | WO 2010/049379 | 5/2010 |
| WO | WO 2010/070090 | 6/2010 |
| WO | WO 2011/003938 | 1/2011 |
| WO | WO 2011/009873 | 1/2011 |
| WO | WO 2011/010324 | 1/2011 |

OTHER PUBLICATIONS

Kirk-Othmer Encyclopedia of Chemical Technology, article:Pharmaceuticals, Large-Scale Synthesis, p. 1-12, published online May 13, 2005.*
U.S. Appl. No. 12/283,022, filed Sep. 8, 2008, Sterling et al.
U.S. Appl. No. 12/283,107, filed Sep. 8, 2008, Sterling et al.
U.S. Appl. No. 12/283,105, filed Sep. 8, 2008, Sterling et al.
U.S. Appl. No. 12/455,969, filed Jun. 10, 2009, Frenkel et al.
U.S. Appl. No. 12/456,642, filed Jun. 19, 2009, Anton Frenkel.
U.S. Appl. No. 12/456,029, filed Jun. 9, 2009, Safadi et al.
U.S. Appl. No. 12/456,031, filed Jun. 9, 2009, Safadi et al.
U.S. Appl. No. 12/455,976, filed Jun. 9, 2009, Safadi et al.
U.S. Appl. No. 12/456,001, filed Jun. 9, 2009, Safadi et al.
Jul. 8, 2009 Office Action issued in U.S. Appl. No. 12/002,082.
May 2, 2008 International Search Report for PCT International Application No. PCT/US07/025583.

(Continued)

Primary Examiner — Brian J Davis
(74) Attorney, Agent, or Firm — John P. White; Cooper & Dunham LLP

(57) ABSTRACT

Disclosed is crystalline R(+)-N-propargyl-1-aminoindan containing water at an amount of less than 0.5% by weight and a pharmaceutical composition comprising the same, and the process for the manufacture and the validation thereof. Also disclosed is a process for the preparation of solid rasagiline base.

17 Claims, 5 Drawing Sheets

OTHER PUBLICATIONS

Jun. 16, 2009 International Preliminary Report on Patentability and the Written Opinion of the International Searching Authority for Internat'l Appln. No. PCT/US07/025583.

U.S. Appl. No. 12/655,827, filed Jan. 8, 2010 (Frenkel, et al.) (including specification and pending claim set).

U.S. Appl. No. 12/655,828, filed Jan. 8, 2010 (Frenkel, et al.) (including specification and pending claim set).

U.S. Appl. No. 12/901,281, filed Oct. 8, 2010 (Lorenzl).

U.S. Appl. No. 12/974,769, filed Dec. 21, 2010 (Frenkel et al.).

Oct. 5, 2009 International Search Report for International Application No. PCT/US2009/03670.

Dec. 21, 2010 International Preliminary Report on Patentability and Written Opinion of the International Searching Authority for Application No. PCT/US2009/03670.

* cited by examiner

US 7,968,749 B2

PROCESS FOR PREPARING AND DRYING SOLID RASAGILINE BASE

The application claims benefit of U.S. Provisional Application No. 61/132,487, filed Jun. 19, 2008, the contents of which are hereby incorporated by reference.

Throughout this application various publications and published patents are referenced. The disclosures of these publications in their entireties are hereby incorporated by reference into this application in order to more fully describe the state of the art to which this invention pertains.

BACKGROUND OF THE INVENTION

R(+)-N-propargyl-l-aminoindan ("R-PAI"), also known as rasagiline, has been reported to be a selective inhibitor of the B-form of the enzyme monoamine oxidase ("MAO-B") and is useful in treating Parkinson's disease and various other conditions.

Rasagiline mesylate is approved for treating Parkinson's disease either as monotherapy or as an adjunct with other treatments. See, e.g. AGILECT®, Physician's Desk Reference (2007), 61$^{st}$ Edition, Thomson Healthcare.

A synthesis of rasagiline is disclosed in U.S. Pat. No. 5,532,415 in which example 3 describes recovery of rasagiline base as an oil after chromatographic separation. The other synthetic examples in U.S. Pat. No. 5,532,415 show rasagiline salt preparation from its crude form or its racemic form which is further reacted with appropriate acids to form pharmaceutically acceptable salts.

In pharmaceutical compositions, crystallinity is a desirable property in an active pharmaceutical ingredient. Crystal substance allow for ease in processing and formulating into most types of pharmaceutical dosage forms. Rasagiline base may be isolated in a crystalline form.

The solid rasagiline base prepared by crystallization is typically not completely "dry" and does contain solvent. There is a need for a method suitable for drying solid rasagiline base from solvent while minimizing loss of yield due to sublimation.

SUMMARY OF THE INVENTION

The subject invention provides crystalline R(+)-N-propargyl-l-aminoindan containing water at an amount of less than 0.5% by weight.

The subject invention also provides a pharmaceutical composition comprising R(+)-N-propargyl-l-aminoindan containing water at an amount of 0.5% by weight and a pharmaceutically acceptable carrier.

The subject invention also provides a process for drying solid R(+)-N-propargyl-l-aminoindan comprising exposing the solid R(+)-N-propargyl-l-aminoindan to a temperature of less than 40° C. and a pressure of between 2-1013.3 mbar for an amount of time suitable to dry the solid R(+)-N-propargyl-l-aminoindan.

The subject invention also provides a process for preparing a pharmaceutical composition comprising crystalline R(+)-N-propargyl-l-aminoindan containing water at an amount of 0.5% by weight and a pharmaceutically acceptable carrier, comprising: a) drying solid R(+)-N-propargyl-l-aminoindan at a temperature of less than 40° C. and a pressure of between 2-1013.3 mbar for an amount of time suitable to dry the solid R(+)-N-propargyl-l-aminoindan; and b) combining the dried R(+)-N-propargyl-l-aminoindan recovered in step a) with the pharmaceutically acceptable carrier, thereby preparing the pharmaceutical composition.

The subject invention also provides a process for producing a validated batch of a drug product containing crystalline R(+)-N-propargyl-l-aminoindan and at least one pharmaceutically acceptable carrier for distribution comprising: a) producing a batch of the drug product; b) determining the water content by weight in the sample of batch; and c) validating the batch for distribution only if the crystalline R(+)-N-propargyl-l-aminoindan in the batch contains less than 0.5% water by weight.

The subject invention also provides a process for producing crystalline R(+)-N-propargyl-l-aminoindan comprising:
 a) purifying a salt of R(+)-N-propargyl-l-aminoindan;
 b) dissolving the purified salt of R(+)-N-propargyl-l-aminoindan in water to form a solution;
 c) cooling said solution to a temperature of 0-15° C.;
 d) basifying said solution to a pH of 9.5-12.5 to form a suspension; and
 e) separating said crystalline rasagiline R(+)-N-propargyl-l-aminoindan from the suspension.

The subject invention also provides a process for producing crystalline R(+)-N-propargyl-l-aminoindan comprising:
 a) obtaining a solution of R(+)-N-propargyl-l-aminoindan in a water-soluble organic solvent;
 b) combining the solution with water;
 c) cooling said solution to between 0 and 20° C. to form crystalline R(+)-N-propargyl-l-aminoindan;
 d) isolating the crystalline R(+)-N-propargyl-l-aminoindan; and
 e) repeating steps a)-d) if the amount of S(+)-N-propargyl-l-aminoindan is more than 0.1 wt % relative to the total amount of R(+)-N-propargyl-l-aminoindan obtained in step d).

DETAILED DESCRIPTION OF THE INVENTION

Figure 1:
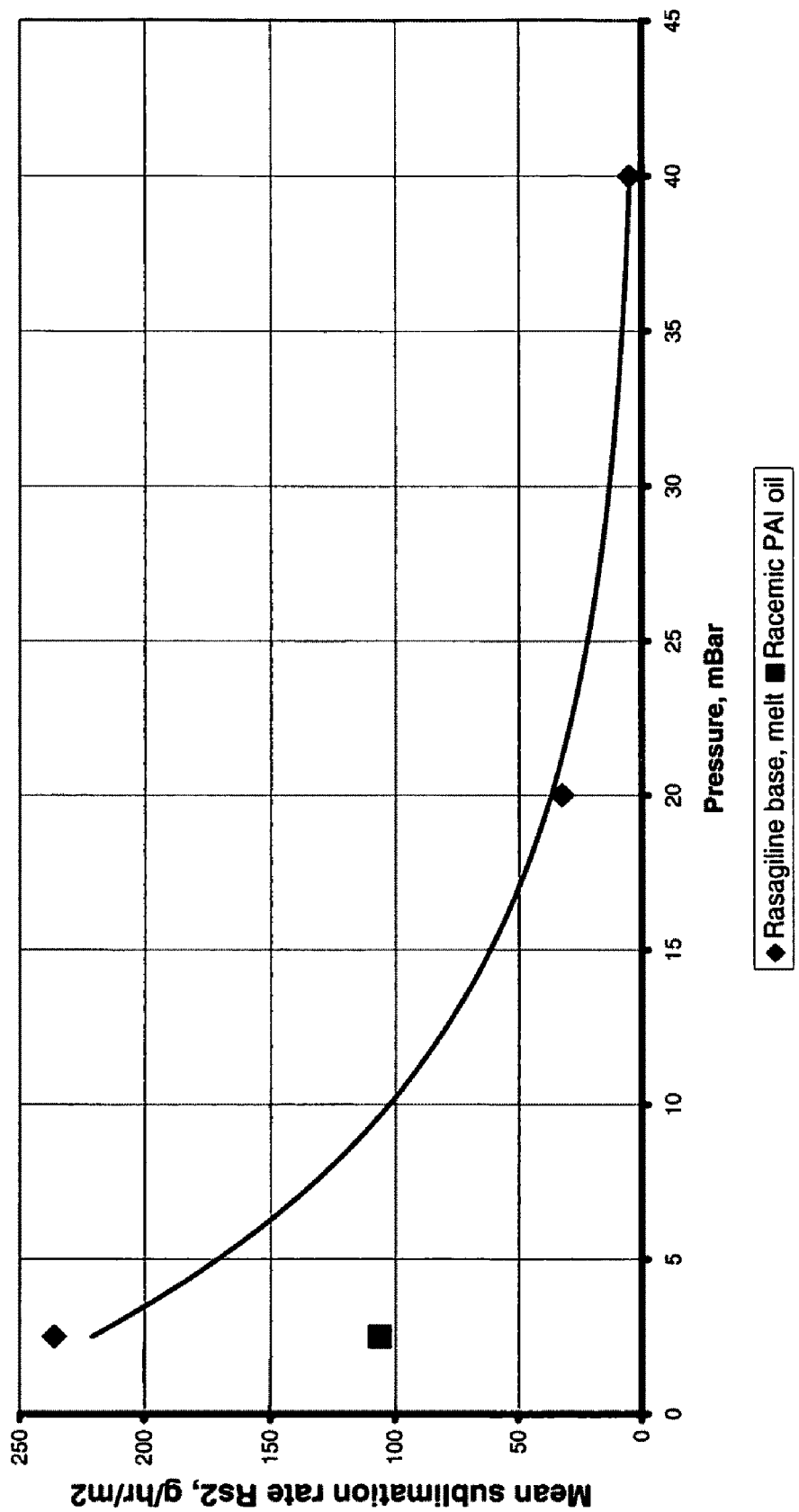
FIG. 1 shows the effect of pressure on evaporation/sublimation rate of liquid rasagiline base at 60° C.

Due to the low melting point and its ability to sublime, drying of solid rasagiline by routine techniques has been observed to result in loss of yield.

Provided herein is a method of drying solid rasagiline base from solvent under conditions which minimize loss of yield due to sublimation.

The subject invention provides crystalline R(+)-N-propargyl-l-aminoindan containing water at an amount of less than 0.5% by weight.

In one embodiment, the crystalline R(+)-N-propargyl-l-aminoindan contain water at an amount of no more than 0.06% by weight.

The subject invention also provides a pharmaceutical composition comprising R(+)-N-propargyl-l-aminoindan containing water at an amount of 0.5% by weight and a pharmaceutically acceptable carrier.

In one embodiment, the pharmaceutical composition is formulated for oral administration. In another embodiment, the pharmaceutical composition is formulated for transdermal application. In yet another embodiment, the pharmaceutical composition is in the form of a transdermal patch.

The subject invention also provides a process for drying solid R(+)-N-propargyl-l-aminoindan comprising exposing the solid R(+)-N-propargyl-l-aminoindan to a temperature of less than 40° C. and a pressure of between 2-1013.3 mbar for an amount of time suitable to dry the solid R(+)-N-propargyl-l-aminoindan.

In one embodiment, the drying chamber is heated to less than 40° C. In another embodiment, the drying chamber is heated to less than 35° C. In yet another embodiment, the drying chamber is heated to less than 25° C. In yet another embodiment, the drying chamber is heated to less than 22° C.

In one embodiment, the pressure at the drying chamber is between 2-1013.3 mbar. In another embodiment, the pressure at the drying chamber is between 3-500 mbar. In yet another embodiment, the pressure at the drying chamber is between 5-250 mbar. In yet another embodiment, the pressure at the drying chamber is between 10-100 mbar. In yet another embodiment, the pressure at the drying chamber is between 20-50 mbar. In yet another embodiment, the pressure at the drying chamber is between 22-28 mbar. In yet another embodiment, the pressure at the drying chamber is between 20-25 mbar. In yet another embodiment, the pressure at the drying chamber is between 2-3 mbar. In yet another embodiment, the pressure at the drying chamber is between 4-5 mbar. In yet another embodiment, the pressure at the drying chamber is between 2-5 mbar.

In embodiment, the drying chamber is heated to less than 40° C. and the pressure at the drying chamber is between 2-1013.25 mbar. In another embodiment, the drying chamber is heated to less than 35° C. and the pressure at the drying chamber is between 20-50 mbar. In yet another embodiment, the drying chamber is heated to less than 35° C. and the pressure at the drying chamber is between 22-28 mbar. In yet another embodiment, the drying chamber is heated to less than 35° C. and the pressure at the drying chamber is between 20-25 mbar. In yet another embodiment, the drying chamber is heated to less than 25° C. and the pressure at the drying chamber is between 22-28 mbar. In yet another embodiment, the drying chamber is heated to less than 25° C. and the pressure at the drying chamber is between 20-25 mbar.

In another embodiment, the amount of time for drying is at least 45 hours.

By a temperature of less than 40° C., it is meant that all tenth and integer degrees Celsius within the range are specifically disclosed as part of the invention. Thus, 39.9, 39.8, 39.7° C., ..., and 39, 38, 37° C., ..., and so on are disclosed as embodiments of this invention. Similarly, by a pressure between 2-1013.3 mbar, it is meant that all tenth and integer percentages within the range are specifically disclosed as part of the invention. Thus, 2.1, 2.2, 2.3 ... 1013.2, 1013.2, 1013.3 are included as embodiments of this invention.

The subject invention also provides a process for preparing a pharmaceutical composition comprising crystalline R(+)-N-propargyl-l-aminoindan containing water at an amount of 0.5% by weight and a pharmaceutically acceptable carrier, comprising: a) drying solid R(+)-N-propargyl-l-aminoindan at a temperature of less than 40° C. and a pressure of between 2-1013.3 mbar for an amount of time suitable to dry the solid R(+)-N-propargyl-l-aminoindan; and b) combining the dried R(+)-N-propargyl-l-aminoindan recovered in step a) with the pharmaceutically acceptable carrier, thereby preparing the pharmaceutical composition.

Additional embodiments of this process are described throughout the specification.

The subject invention also provides a process for producing a validated batch of a drug product containing crystalline R(+)-N-propargyl-l-aminoindan and at least one pharmaceutically acceptable carrier for distribution comprising: a) producing a batch of the drug product; b) determining the water content by weight in the sample of batch; and c) validating the batch for distribution only if the crystalline R(+)-N-propargyl-l-aminoindan in the batch contains less than 0.5% water by weight.

In one embodiment, the batch is validated only if the crystalline R(+)-N-propargyl-l-aminoindan in the batch contains less than 0.06% water by weight.

The subject invention also provides a process for producing crystalline R(+)-N-propargyl-1-aminoindan comprising:
 f) purifying a salt of R(+)-N-propargyl-1-aminoindan;
 g) dissolving the purified salt of R(+)-N-propargyl-1-aminoindan in water to form a solution;
 h) cooling said solution to a temperature of 0-15° C.;
 i) basifying said solution to a pH of 9.5-12.5 to form a suspension; and
 j) separating said crystalline rasagiline R(+)-N-propargyl-1-aminoindan from the suspension.

In one embodiment of the process, step a) comprises:
 i) dissolving the salt of R(+)-N-propargyl-1-aminoindan in water to form a solution;
 ii) adding a water-soluble organic solvent to the solution;
 iii) cooling the solution to a temperature of about 0-10° C.; and
 iv) obtaining the purified salt of R(+)-N-propargyl-1-aminoindan from the suspension.

In another embodiment of the process, the purified salt of R(+)-N-propargyl-1-aminoindan obtained in step iv) is of enhanced optical purity relative to the R(+)-N-propargyl-1-aminoindan prior to crystallization.

In another embodiment of the process, the salt of R(+)-N-propargyl-1-aminoindan is a tartrate salt.

The subject invention also provides a process for producing crystalline R(+)-N-propargyl-1-aminoindan comprising:
 a) obtaining a solution of R(+)-N-propargyl-1-aminoindan in a water-soluble organic solvent;
 b) combining the solution with water;
 c) cooling said solution to between 0 and 20° C. to form crystalline R(+)-N-propargyl-1-aminoindan;
 d) isolating the crystalline R(+)-N-propargyl-1-aminoindan; and
 e) repeating steps a)-d) if the amount of S(+)-N-propargyl-1-aminoindan is more than 0.1 wt % relative to the total amount of R(+)-N-propargyl-1-aminoindan obtained in step d).

In one embodiment of the process, the water-soluble organic solvent is an alcohol.

In another embodiment of the process, the alcohol is either ethanol or isopropanol or a mixture of ethanol and isopropanol.

In another embodiment of the process, the crystalline R(+)-N-propargyl-1-aminoindan is of enhanced optical purity relative to the R(+)-N-propargyl-1-aminoindan prior to crystallization.

As used herein, "PAI" refers to N-propargyl-1-aminoindan.

As used herein, "drug substance" refers to the active ingredient in a drug product, which provides pharmacological activity or other direct effect in the diagnosis, cure, mitigation, treatment, or prevention of disease, or to affect the structure of any function of the body of man or animals.

As used herein, "drug product" refers to a pharmaceutical composition in finished dosage form containing the drug substance as well as at least one pharmaceutically acceptable carrier.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life.

R(+)-N-propargyl-1-aminoindan can be obtained in the crystalline form characterized by a powder X-ray diffraction pattern having peaks at 8.5, 12.6, 16.1, and 16.9 in degrees two theta±0.2. It can be further characterized by an X-ray powder diffraction pattern having peaks at 20.3, 20.9, 25.4, 26.4, and 28.3 in degrees two theta±0.2; or by a melting point of 38-41° C.

A process for the manufacture of crystalline R(+)-N-propargyl-1-aminoindan comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

Another process for the manufacture of crystalline R(+)-N-propargyl-1-aminoindan comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a second residue; and e) maintaining the second residue at a temperature between 0 and 25° C. to form crystalline R(+)-N-propargyl-1-aminoindan.

Yet another process for the manufacture of crystalline R(+)-N-propargyl-1-aminoindan comprises a) obtaining a solution of R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan.

Crystalline rasagiline base has lower water solubility than many rasagiline salts, especially the mesylate salt, which is water soluble. The solubility of rasagiline mesylate in water is 92 mg/ml at a pH of 6.7 and 570 mg/ml at a pH of 3.3, both measured at 25° C. At the same temperature, the solubility of rasagiline base in water is 5.5 mg/ml at a pH of 11.

Crystalline rasagiline base may be used as a synthetic intermediate to be used to attain a rasagiline salt, such as rasagiline mesylate or rasagiline tartrate. The crystalline rasagiline base may be dissolved in a solvent and reacted with an acid to form a pharmaceutically acceptable acid addition salt. The crystallization of rasagiline base could provide additional purification of the acid addition salt.

Water solubility is often an important characteristic of an active pharmaceutical ingredient, especially when formulating oral compositions. Sometimes, lipophilicity of an active pharmaceutical ingredient is desired when formulating other pharmaceutical compositions. Crystalline rasagiline base may be useful for formulating pharmaceutical compositions wherein low solubility in water is desired. For example, compositions for transdermal administrations can be formulated from lipophilic compounds. Examples of such transdermal compositions include ointments, creams and patches.

Specific examples of pharmaceutical acceptable carriers and excipients that may be used to formulate oral dosage forms are described, e.g., in U.S. Pat. No. 6,126,968 to Peskin et al., issued Oct. 3, 2000. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

U.S. Pat. No. 6,126,968, the entire contents of which are incorporated herein by reference, disclosed that the stability of formulations comprising PAI can be significantly improved by the incorporation of relatively large amounts of certain alcohols. In particular, the alcohol is selected from the group of pentahydric or hexahydric alcohols (U.S. Pat. No. 6,126,968). The alcohol is typically selected from mannitol, xylitol or sorbitol (U.S. Pat. No. 6,126,968). The composition may further comprise citric acid (U.S. Pat. No. 6,126,968).

(R)-PAI itself may be prepared, for example, according to the process described in Example 6B of WO 95/11016.

Transdermal Formulations and Transdermal Patches

Transdermal Formulations are medicated adhesive patches placed on the skin to deliver a time-released dose of medication through the skin and into the bloodstream. A wide variety of pharmaceuticals can be delivered through transdermal patches, such as nicotine for smoking cessation, scopolamine for motion sickness, estrogen for menopause, and prevention of osteoporosis, nitroglycerin for angina, lidocaine for pain relief from shingles. Some pharmaceuticals must be combined with other substances, such as alcohol, to increase their ability to penetrate the skin. Molecules of insulin, and many other pharmaceuticals, however, are too large to pass through the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. ("Transdermal Patches" Wikipedia, Nov. 15, 2007, Wikipedia Foundation, Inc., Dec. 13, 2007 http://en.wikipedia.org/wiki/Transdermal_patch; and Remington, The Science and Practice of Pharmacy, 20$^{th}$ Edition, 2000)

In reservoir type patches, a drug is combined with a non-volatile, insert liquid, such as mineral oil, whereas drug in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST PRESENT, FUTURE," Molecular Interventions, 4:308-312).

The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Deliver)

Rasagiline may also be used in combination with other drug in a transdermal patch, such as Levodopa, L-carbidopa, beserazide, ladostigil, or riluzole.

EXPERIMENTAL DETAILS

Set 1: Initial Preparation of Rasagiline Crystals

Example 1

Isolation of Rasagiline Base by Splitting and Extraction

Rasagiline mesylate was prepared essentially as described in U.S. Pat. No. 5,532,415 example 6B, with the exception that the tartrate salt was split by addition of NaOH, and the rasagiline free base was isolated as an oil. The mesylate salt was then formed by addition of methanesulfonic acid.

120 g of rasagiline mesylate were dissolved in 700 ml of deionized water. 400 ml of toluene were added and the mixture was basified with 25% NaOH solution to a pH of about 14. After stirring, two phases separated. The lower water phase was extracted with 200 ml of toluene. The phases were allowed to separate and the aqueous phase was discarded.

The two toluenic extractions were combined and the solvent was distilled under vacuum. The yield of rasagiline base was 88.5 g of a yellowish oil with a melting point of below 20° C.

25.1 g of the liquid rasagiline base was sampled. The sample was mixed with ethanol and the solvent was distilled under vacuum. 22.6 g of the rasagiline base residue, in the form of a yellowish oil remained after the ethanol evaporation. The rasagiline base in oil form remained in oil form for a number of weeks, and did not crystallize spontaneously.

Example 2

Isolation of Rasagiline Base by Splitting and Extraction 155 g of rasagiline tartrate, prepared essentially as described in U.S. Pat. No. 5,532,415 example 6B, and 20 g of rasagiline mesylate, prepared as described in example 1, were dissolved in 800 ml of water. 400 ml of toluene were added to the solution and the mixture was basified with 25% NaOH solution to a pH of about 14 and heated to 45±5° C.

After stirring, two phases were separated. The lower water phase was extracted twice with 300 ml of toluene at 45±5° C. The organic phases were combined and the aqueous phase was discarded.

The combined organic phase was washed with 200 ml of deionized water. Then the solvent was distilled under vacuum and 50 ml isopropanol were added to the resulting residue. The solvent was removed by vacuum and additional 50 ml isopropanol were added and then removed by vacuum. 100 g of syrup-like liquid rasagiline base were formed.

Example 3

Splitting and Spontaneous Crystallization from Water 15 g of rasagiline mesylate were dissolved in 150 ml water while stirring. The solution was cooled to 5° C. and 25% NaOH solution was added slowly. During the addition, batch temperature was maintained between 3 and 5° C. Solid precipitation was observed after reaching a pH of 7.5. After reaching a pH of 11, the NaOH addition was stopped, the batch was stirred while cooling for one hour and filtered. The filtration proceeded quickly. The solid product was washed with water on the filter and dried under vacuum.

8.8 g of solid dried rasagiline base were attained. The yield was 91.6%. The melting point of the solid was determined to be 38.2-38.4° C.

Example 4

Melt Crystallization 6 g of rasagiline base liquid in syrup-like form, from example 1, after toluenic evaporation were dissolved in 20 ml of isopropanol. The solution was evaporated in a warm water bath using a rotating evaporator under 12 mbar vacuum until complete solvent removal. The residue was then dissolved in an additional 20 ml of isopropanol and the evaporation was repeated. The resulting residue crystallized spontaneously at room temperature after a few hours. The solid crystalline residue was determined to be rasagiline base. 5.2 g of the solid crystalline base were attained. The yield was quantitative.

Example 5

Addition of Rasagiline Ethanolic Solution to Water 2.4 g of rasagiline base from example 1 were dissolved in 2.4 g of ethanol. The solution was added drop-wise to 5 ml of cold (0-5° C.) water while stirring, and a white precipitate was formed during the addition. The resulting mixture was stirred while cooling for about 30 minutes and was filtered. The filtration proceeded quickly, and the solid product was dried to constant mass under vacuum.

2.15 g of solid crystalline rasagiline were attained, with a yield of 89.6%.

Analysis: Chromatographic purity by HPLC ~100%, Assay by HPLC—99.0%.

Example 6

Addition of Water to Rasagiline Ethanolic Solution 3 g of rasagiline base from example 1 were dissolved in 5 ml of ethanol. The solution was stirred at room temperature and 4.5 ml of water were added. No precipitation occurred. The resulting solution was cooled, and at 12° C. precipitation of a white material was observed. The mixture was cooled to ~0° C., stirred at this temperature for 30 min, and filtered. The filtration proceeded quickly. The solid product was washed with water on the filter and was dried under vacuum.

2.72 g of solid crystalline rasagiline were attained, with a yield of 90.0%.

Analysis: Chromatographic purity by HPLC ~100%, Assay by HPLC—100.0%.

Example 7

Addition of Rasagiline Isopropanolic Solution to Water 8.2 g of rasagiline base from example 1 were dissolved in 10 ml of isopropanol and the solution was stirred at room temperature. 14 ml of water were added. No precipitation occurred. The resulting solution was cooled, and at 17° C. precipitation of white material was observed. 20 ml of deionized water were added to the mixture and the mixture was further cooled to ~0° C., stirred at this temperature for 30 min, and filtered.

The filtration proceeded quickly. The solid product was washed with water on the filter and dried under vacuum. 5.96 g of solid crystalline rasagiline were attained, with a yield of 72.7%.

Analysis: Chromatographic purity by HPLC ~100%, Assay by HPLC—99.7%

Example 8

Addition of Water to Rasagiline Isopropanolic Solution

Crop A 148 g of rasagiline base (48.0 g from example 1, and 100.0 g from example 2) were dissolved in 180 ml of isopropanol. The solution was cooled to 17° C. and 252 ml of deionized water were added at this temperature. The solution was cooled to 10° C. and seeded with solid rasagiline base. Immediate crystallization was observed. 100 ml of water were then added to the mixture. The mixture was cooled to 1° C., stirred at this temperature for 30 min and filtered. The solid was washed on the filter with 200 ml of water and dried under vacuum.

138.9 g of solid, crystalline rasagiline were attained, with a yield of 93.8%. The melting point in an open capillary was determined to be 39.0-39.2° C.

Analysis: Chromatographic purity by HPLC ~100%, Assay by HPLC—98.5%.

Crop B

The mother liquor and washing liquor from crop A were combined, and solid product precipitated from the mixture. Yellowish material was separated by filtration and dried under vacuum.

1.5 g of solid, crystalline rasagiline base were attained, with a yield of 1.0%.

Discussion

The solid crystalline rasagiline base which was synthesized in examples 3-8 was found to be of high purity.

The same melting point value (41° C. by differential scanning calorimetry (DSC) or 38-40° C. in an open capillary) was measured for all batches of the crystalline rasagiline base. Low levels of volatiles (water and residual solvents) were found by Karl Fischer (KF) and by thermogravimetric analysis (TGA) methods. This indicated that crystalline rasagiline base is not hygroscopic.

Crystalline rasagiline base was found freely soluble in polar and non-polar organic solvents—alcohols, acetone, ethyl acetate, toluene, diethyl ether, dioxane, hexane and n-heptane.

All batches of solid rasagiline base were found highly crystalline by powder X-ray diffraction (XRD) and DSC method. Characteristic XRD and Fourier Transfer Infrared (FTIR) patterns and reproducible narrow melting range and enthalpy show the same polymorphic composition of all experimental batches from examples 3-8. The crystal form was designated as Form I.

The X-Ray Diffraction equipment used was a Scintag X-Ray powder diffractometer model X'TRA, Cu-tube, solid state detector.

Sample holder: a round standard aluminum sample holder with round zero background quartz plate with cavity of 25 (diameter)*0.5 (dept.) mm.

Scanning parameters: Range: 2-40 degrees two-theta.
Scan mode: Continuous scan
Step size: 0.05 deg.
Rate: 5 deg./min.

The peaks of a sample prepared according to Example 4 are listed below. The most characteristic peaks are listed in bold.

| Form I |
|---|
| 8.5 |
| 12.6 |
| 16.1 |
| 16.9 |
| 20.3 |
| 20.9 |
| 25.4 |
| 26.4 |
| 28.3 |

FTIR analysis of the samples was performed as follows:

Equipment: Perkin Elmer Spectrum One FT-IR Spectrometer S/N 58001.

Parameters: The samples were studied in DRIFT mode. All the spectra were measured in 16 scans. Resolution: 4.0 cm$^{-1}$.

All samples of solid rasagiline base prepared in this study appear as white crystalline powder (with the exception of Crop B from example which was isolated as a yellowish powder.) Microscopic observation shows that the crystallization conditions strongly affect the particle size and morphology. Seeded crystallization provides large regular non-aggregated crystals while spontaneous precipitation resulted in formation of small aggregated particles. The difference in the particle morphology is not related to polymorphism.

The morphology and particle size of the crystalline rasagiline base from the examples above is shown in the table below. The morphology and particle size was determined by microscopic observation.

| Example | Morphology | Particle Size Range (μm) |
|---|---|---|
| 4 | Irregular particles | 250-1000 |
| 5 | Small rods | 5-50 |
| 6 | Rods | 30-150 |
| 7 | Small aggregated rods | 5-50 |
| 8 | Rods | 250-2000 |

Starting Materials for Examples 9, 10 and 11:
(1) Wet Rasagiline Hemi Tartrate containing ~10-15% residual solvent and 0.7% S-isomer.
(2) Racemic RAI base, oil, PAI content—94% by HPLC.

Example 9

Splitting and Precipitation from Isopropanol-Water, Seeded Emulsion Crystallization 70.0 g of Rasagiline Tartrate salt (1) suspended in 320 ml deionized water at stirring. The suspension heated to 45° C. and 31 ml of 25% NaOH solution was added with 160 ml Toluene. The mixture was stirred and the resulting emulsion was settled. Two phases were separated. The lower aqueous phase (pH=13-14) was discarded. The upper toluenic phase was washed with 100 ml deionized water at 45° C. and settled. Lower aqueous phase (pH=9-10) was discarded.

Toluenic solution was evaporated under vacuum in evaporator, after the solvent evaporation completion 50 ml isopropanol was added to the residue and evaporation was continued.

After completion of the evaporation 25 ml of isopropanol was added and distilled out under the same conditions.

The residue, oil of R-PAI base (33.9 g), was dissolved in 41 ml isopropanol.

The solution was cooled to 15° C. and 58 ml of deionized water was added by portions in 2 hr at cooling and stirring. During the addition of water oily precipitate was formed. The resulting emulsion of oil in water was stirred at 1-3° C. for one hour, no crystallization was observed.

The batch was seeded with crystalline Rasagiline base at 1-3° C. and immediate exothermic crystallization took place. 50 ml of water was added to the resulting slurry to improve stirrability and flowability. The batch was stirred for additional 30 minutes and filtered. The solid was washed with water and dried at room temperature under vacuum.

31.5 g of solid dry R-PAI base were attained, with a yield of 92% on oil base. FIG. 11 is a micrograph of this rasagiline base.

Analysis: Melting point (by DSC)—40.8° C., S-isomer by HPLC 0.02%, Purity by HPLC—100%, Assay by HPLC—98%.

Example 10

Splitting and Precipitation from Isopropanol-Water, Seeded Crystallization from Solution Isopropanol-Water 100.0 g of Rasagiline Tartrate (1) was suspended in 458 ml deionized water, 229 ml Toluene was added and 46 ml of 25% NaOH solution was introduced at stirring. The mixture was heated to 45° C., stirred at 45 C for 15 minutes and settled at this temperature.

Two phases were separated. The lower aqueous phase (pH=13-14) was discarded, the upper toluenic phase was washed with 140 ml deionized water. The resulting emulsion was settled, and two phases were separated. The lower aqueous phase (pH=9-10) was discarded, the toluenic solution was evaporated under vacuum in evaporator.

After the solvent evaporation completion 60 ml isopropanol was added to the residue and evaporation was continued.

After completion of the evaporation 50 ml of isopropanol was added and distilled out under the same conditions.

The residue, oil of R-PAI base (46.4 g), was dissolved in 56 ml isopropanol.

The solution was cooled to 16° C. and 147.5 ml of deionized water was added by portions in 3 hr at cooling and stirring. During the addition of water precipitation development was observed and the batch was immediately seeded with crystalline R-PAI base.

The resulting suspension was cooled to 2° C., stirred at this temperature overnight and filtered. The solid was washed with water and dried at room temperature under vacuum.

48.1 g of Solid dry R-PAI base were attained, with a yield of 96% on oil base. FIG. 12 is a micrograph of this rasagiline base.

Analysis: Melting point (by DSC)—41.3° C., S-isomer by HPLC 0.01%, Purity by HPLC—100%, Assay by HPLC—96%

Example 11

Racemic PAI Base Crystallization (AF-8026) Precipitation from Isopropanol-Water 51.0 g of racemic PAI base oil (2) dissolved in 50 ml isopropanol. The solvent was distilled out of the solution under vacuum at evaporator.

The residue (49.4 g) was dissolved in 60 ml isopropanol, stirred and cooled. 156 ml of deionized water was added by portions in 3 hr at cooling and stirring. During the addition of water oily precipitate was formed. The batch was seeded with crystalline Rasagiline base, no crystallization was observed.

The resulting emulsion of oil in water was stirred at 3° C. for 1 hour, no crystallization was observed.

The batch was crystallized spontaneously during stirring overnight at 1° C. The solid was filtered, but during the filtration it began to melt. At room temperature the solid product completely liquefied on the filter in 1-2 min.

The material was sampled before the melting completion.
Analysis: S-isomer by HPLC 49.4%, Assay by HPLC—87%.

Discussion

Examples 9, 10 and 11 presented above show that the ability to crystallize at room temperature is an intrinsic property of pure Rasagiline base (R-isomer). Racemic PAI base exists at room temperature only in liquid form, its melting point being between 1 and 18° C. (Example 11).

The Examples also show that crystallization of Rasagiline base contaminated with S-isomer provides significant purification of the crystallized product. Starting material containing 0.7% of S-isomer was processed into solid crystalline Rasagiline base with only 0.01-0.02% of S-isomer.

Examples 9, 10 and 11 also show the same trend in Particle Size of the crystallized product as was described in previous Examples. The slow seeded crystallization at 10-16° C. (Example 9) provides higher particle size of Rasagiline base than emulsion crystallization at 1-3° C. (Example 10).

Conclusions

The above experiments demonstrate varying processes for manufacturing crystalline R(+)-N-propargyl-1-aminoindan.

The first process for manufacture of crystalline R(+)-N-propargyl-1-aminoindan comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

Another process for manufacture of crystalline R(+)-N-propargyl-1-aminoindan comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a residue; and e) maintaining the second residue at a temperature between 0 and 25° C. to form crystalline R(+)-N-propargyl-1-aminoindan.

Yet another process for manufacture of crystalline R(+)-N-propargyl-1-aminoindan comprises: a) obtaining a solution of crystalline R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan.

The resulting crystalline R(+)-N-propargyl-1-aminoindan can be characterized by a powder X-ray diffraction pattern having peaks at 8.5, 12.6, 16.1, and 16.9 in degrees two theta±0.2.

The crystalline rasagiline base can further be characterized by an X-ray powder diffraction pattern having peaks at 20.3, 20.9, 25.4, 26.4, and 28.3 in degrees two theta±0.2.

The crystalline rasagiline base can further be characterized by a melting point of 38-39° C. when determined in an open capillary or 41° C. when determined by differential scanning calorimetry.

However, the crystalline rasagiline base obtained using the foregoing examples were not dry. Accordingly, further drying processing was undertaken.

Experimental Details

Set 2: Drying of Rasagiline and Racemic PAI Base

Examples 12-24 provide sublimation rates of rasagiline base and racemic PAI base under various conditions.

Examples 25-37 provide water content and percent yield of dry product after rasagiline base crystallization and drying.

Crystallization experiments were performed in 100 ml and 250 ml jacketed glass reactors equipped with stirrer, circulating oil bath and thermometer. Liquid additions into the reactor were performed using 25 ml dropping funnel. Solid products were filtered using Büchner filter and dried in vacuum oven in glass trays.

Example 12

Sublimation of Rasagiline Base at 2-3 mbar Pressure and 21° C. Temperature

Approximately four (4) grams of rasagiline base was introduced into the sublimation reservoir of a standard Sigma-Aldrich glass sublimation apparatus, (Cat. No. Z221171-1EA) with internal diameter of 3 cm. The apparatus was equipped with vacuum pump, vacuumeter and circulating ice-water bath for cooling of the apparatus' sublimation head. The apparatus was then closed and circulation of coolant at 0 to 1° C. was started. The vacuum was then built to a pressure ("P") of 2-3 mbar and the reservoir was introduced into thermostatic water bath maintained at temperature ("T") of 21° C.

The process was controlled by visual observation of the sublimed solid forming on the sublimation head. After sublimation completed the operation time was recorded, the apparatus was opened and the sublimed solid was removed from the head and weighed.

The mean sublimation rate was calculated as follows:

Mean sublimation rate $R_{s1}$:

$$R_{s1}=m/M \cdot t \; [\text{g g}^{-1} \text{ hr}^{-1}]$$

Mean sublimation rate $R_{s2}$:

$$R_{s2}=m/S \cdot t \; [\text{g m}^{-2} \text{ hr}^{-1}]$$

Mean relative sublimation rate R:

$$R=m \cdot 100/M \cdot t \; [\%/\text{hr}]$$

m—mass of sublimed material, g
M=mass of starting material, g
t=sublimation time, hrs
S=sublimation area (apparatus section area), $m^2$ After 8 hours, 10 mg of sublimed rasagiline were attained, with a yield of 0.25%. The mean sublimation rates were $R_{s1}=3.12 \times 10^{-5}$ g $g^{-1}$ $hr^{-1}$; $R_{s2}=1.333$ g $m^{-2}$ $hr^{-1}$; and R=0.0312%/hr.

Example 13

Sublimation of Rasagiline Base at 2-3 mbar Pressure and 35° C. Temperature

The experimental steps from Example 1 was used with the exception that T=35° C.

After 5.33 hours, 25 mg of sublimed rasagiline were attained, with a yield of 0.62%. The mean sublimation rates were $R_{s1}=1.17 \times 10^{-3}$ g $g^{-1}$ $hr^{-1}$; $R_{s2}=4.978$ g $m^{-2}$ $hr^{-1}$; and R=0.116%/hr.

Example 14

Sublimation of Rasagiline Base at 2-3 mbar Pressure and 60° C. Temperature

The experimental steps from Example 1 was used with the exception that T=60° C. At 60° C., starting rasagiline was liquid (melt).

After 4.0 hours, 890 mg of sublimed rasagiline were attained, with a yield of 22.4%. The mean sublimation rates were $R_{s1}=5.62 \times 10^{-2}$ g $g^{-1}$ $hr^{-1}$; $R_{s2}=236.19$ g $m^{-2}$ $hr^{-1}$; and R=5.6%/hr.

Example 15

Sublimation of Rasagiline Base at 20 mbar Pressure and 21° C. Temperature

The experimental steps from Example 1 was used with the exception that P=20 mbar.

After 8.5 hours, 0 mg of sublimed rasagiline were attained, with a yield of 0.0%. The mean sublimation rates were $R_{s1}=0.0$ g $g^{-1}$ $hr^{-1}$; $R_{s2}=0.0$ g $m^{-2}$ $hr^{-1}$; and R=0.0%/hr.

Example 16

Sublimation of Rasagiline Base at 40 mbar Pressure and 21° C. Temperature

The experimental steps from Example 1 was used with the exception that P=40 mbar.

After 8.5 hours, 0 mg of sublimed rasagiline were attained, with a yield of 0.0%. The mean sublimation rates were $R_{s1}$=0.0 g g$^{-1}$ hr$^{-1}$; $R_{s2}$=0.0 g m$^{-2}$ hr$^{-1}$; and R=0.0%/hr.

Example 17

Sublimation of Rasagiline Base at 40 mbar Pressure and 35° C. Temperature

The experimental steps from Example 1 was used with the exception that T=35° C. and P=40 mbar.

After 5.33 hours, 8 mg of sublimed rasagiline were attained, with a yield of 0.20%. The mean sublimation rates were $R_{s1}$=3.75×10$^{-4}$ g g$^{-1}$ hr$^{-1}$; $R_{s2}$=1.593 g m$^{-2}$ hr$^{-1}$; and R=0.0375%/hr.

Example 18

Sublimation of Rasagiline Base at 20 mbar Pressure and 35° C. Temperature

The experimental steps from Example 1 was used with the exception that T=35° C. and P=20 mbar.

After 5.33 hours, 11 mg of sublimed rasagiline were attained, with a yield of 0.27%. The mean sublimation rates were $R_{s1}$=5.15×10$^{-4}$ g g$^{-1}$ hr$^{-1}$; $R_{2}$=2.192 g m$^{-2}$ hr$^{-1}$; and R=0.0506%/hr.

Example 19

Sublimation of Rasagiline Base at 40 mbar Pressure and 60° C. Temperature

The experimental steps from Example 1 was used with the exception that T=60° C. and P=40 mbar. At 60° C., starting rasagiline was liquid (melt).

After 5.33 hours, 25 mg of sublimed rasagiline were attained, with a yield of 0.62%. The mean sublimation rates were $R_{s1}$=1.17×10$^{-3}$ g g$^{-1}$ hr$^{-1}$; $R_{s2}$=4.978 g m$^{-2}$ hr$^{-1}$; and R=0.116%/hr.

Example 20

Sublimation of Rasagiline Base at 20 mbar Pressure and 60° C. Temperature

The experimental steps from Example 1 was used with the exception that T=60° C. and P=20 mbar. At 60° C., starting rasagiline was liquid (melt).

After 5.33 hours, 162 mg of sublimed rasagiline were attained, with a yield of 4.1%. The mean sublimation rates were $R_{s1}$=7.64×10$^{-3}$ g g$^{-1}$ hr$^{-1}$; $R_{s2}$=32.26 g m$^{-2}$ hr$^{-1}$; and R=0.769%/hr.

Example 21

Sublimation of Racemic PAI Oil at 20 mbar Pressure and 22° C. Temperature

The experimental steps from Example 1 was used with the exception that the starting material is racemic PAI oil, T=22° C., and P=20 mbar.

After 8 hours, 0 mg of sublimed racemic PAI were attained, with a yield of 0.0%. The mean sublimation rates were $R_{s1}$=0.0 g g$^{-1}$ hr$^{-1}$; $R_{s2}$=0.0 g m$^{-2}$ hr$^{-1}$; and R=0.0%/hr.

Example 22

Sublimation of Racemic PAI Oil at 20 mbar Pressure and 35° C. Temperature

The experimental steps from Example 1 was used with the exception that the starting material is racemic PAI oil, T=35° C., and P=20 mbar.

After 5.33 hours, 0 mg of sublimed racemic PAI were attained, with a yield of 0.0%. The mean sublimation rates were $R_{s1}$=0.0 g g$^{-1}$ hr$^{-1}$; $R_{s2}$=0.0 g m$^{-2}$ hr$^{-1}$; and R=0.0%/hr.

Example 23

Sublimation of Racemic PAI Oil at 2-3 mbar Pressure and 22° C. Temperature

The experimental steps from Example 1 was used with the exception that the starting material is racemic PAI oil and T=22° C.

After 3.0 hours, 10 mg of sublimed racemic PAI were attained, with a yield of 0.25%. The mean sublimation rates were $R_{s1}$=8.33×10$^{-4}$ g g$^{-1}$ hr$^{-1}$; $R_{s2}$=3.537 g m$^{-2}$ hr$^{-1}$; and R=0.08%/hr.

Example 24

Sublimation of Racemic PAI Oil at 2-3 mbar Pressure and 60° C. Temperature

The experimental steps from Example 1 was used with the exception that the starting material is racemic PAI oil and T=60° C.

After 1.3 hours, 130 mg of sublimed racemic PAI were attained, with a yield of 3.25%. The mean sublimation rates were $R_{s1}$=2.50×10$^{-2}$ g g$^{-1}$ hr$^{-1}$; $R_{s2}$=101.16 g m$^{-2}$ hr$^{-1}$; and R=2.5%/hr.

Example 25

Addition of Water to Rasagiline Base Solution in Ethanol

Twenty-three (23) grams of dry rasagiline tartrate reacted with NaOH (20 g 25% solution) in water-toluene mixture (75:95 ml) at stirring. The mixture was settled, the aqueous layer (pH>11) was separated, and organic phase was washed with water and evaporated under vacuum in rotary evaporator. Then 30 ml absolute ethanol was added to the residue and evaporated.

Addition of absolute ethanol and solvent evaporation under vacuum was repeated.

The residue—15.4 g of oil was dissolved in 19.5 ml absolute ethanol at stirring.

The ethanolic solution was stirred and 27 ml water was added at 18-20° C., then the batch was seeded with crystals of solid rasagiline base. Immediate crystallization was observed. The batch was cooled to 10-15° C. and additional 11 ml water was added.

Then the batch was cooled to 0-5° C., stirred at this temperature for 30 minutes and filtered. The solid was washed on the filter with 30 ml of water.

Wet solid (16.0 g) was dried at temperature 25° C. and reduced pressure (4-5 mbar) to constant weight. Water content of the dry product was determined by the Karl Fischer (KF) method.

Water content by KF=0.18%.
Dry product=14.0 g, yield=90.9%.

Example 26

Addition of Water to Rasagiline Base Solution in IPA

Twenty-three (23) grams of dry rasagiline tartrate reacted with NaOH (20 g 25% solution) in water-toluene mixture (75:95 ml) at stirring. The mixture was settled, the aqueous layer was separated, and organic phase was washed with water and evaporated under vacuum in rotary evaporator. Then 30 ml isopropanol was added to the residue and evaporated.

Addition of isopropanol and solvent evaporation under vacuum was repeated.

The residue—16.0 g of oil was dissolved in 19.5 ml isopropanol at stirring.

The solution was stirred and 27 ml water was added at 18-20° C., then the batch was seeded with crystals of solid rasagiline base. Immediate crystallization was observed. The batch was cooled to 10-15° C. and additional 11 ml water was added.

Then the batch was cooled to 0-5° C., stirred at this temperature for 30 minutes and filtered. The solid was washed on the filter with 30 ml of water.

Wet solid (16.9 g) was dried at temperature 25° C. and reduced pressure (4-5 mbar) to constant weight. Water content of the dry product was determined by the Karl Fischer (KF) method.

Water content by KF=0.21%.
Dry product=14.8 g, yield=92.5%.

Example 27

Addition of Rasagiline Base (Oil) to IPA-Water

Twenty-three (23) grams of dry rasagiline tartrate reacted with NaOH (20 g 25% solution) in water-toluene mixture (75:95 ml) at stirring. The mixture was settled, the aqueous layer was separated, and organic phase was washed with water and evaporated under vacuum in rotary evaporator. Then 30 ml isopropanol was added to the residue and evaporated.

Addition of isopropanol and solvent evaporation under vacuum was repeated.

The residue—16.0 g of oil was added to isopropanol-water solution (20:27 ml) at cooling and stirring. During the addition the oil, the temperature was maintained above 40° C. in order to prevent spontaneous crystallization of the free base.

Isopropanol-water solution temperature was maintained within 0-5° C. After addition completion, the mixture was stirred at this temperature for 30 minutes and filtered. The solid was washed on the filter with 30 ml of water.

Wet solid (16.8 g) was dried at 25° C. and reduced pressure (4-5 mbar) to constant weight. Water content of the dry product was determined by the Karl Fischer (KF) method.

Water content by KF=0.06%.
Dry product=13.9 g, yield=86.7%.

Example 28

Addition of Rasagiline Base (Oil) to Cold Water

Twenty-three (23) grams of dry rasagiline tartrate reacted with NaOH (20 g 25% solution) in water-toluene mixture (75:95 ml) at stirring. The mixture was settled, the aqueous layer was separated, and organic phase was washed with water and evaporated under vacuum in rotary evaporator. Then 30 ml isopropanol was added to the residue and evaporated.

Addition of isopropanol and solvent evaporation under vacuum was repeated.

The residue—16.0 g of oil was added to 60 ml of cold water (0-5° C.) at cooling and stirring. During the addition the batch the temperature was maintained below 5° C. After the addition completion the dropping funnel was rinsed with 6 ml of isopropanol and the rinse was introduced into the reactor. Resulting suspension was stirred at 0-5° C. for 30 minutes and filtered.

Significant amount of solid product was found deposed on the stirrer and on the reactor surface, poor slurry homogeneity and flowability were also observed.

The solid product was washed on the filter with 30 ml of water.

Wet solid (15.3 g) was dried at 25° C. and reduced pressure (4-5 mbar) to constant weight. Water content of the dry product was determined by the Karl Fischer (KF) method.

Water content by KF=0.10%.
Dry product=14.1 g, yield=88.2%.

Example 29

Addition of Rasagiline Base Solution in Ethanol to Water

Twenty-three (23) grams of dry rasagiline tartrate reacted with NaOH (20 g 25% solution) in water-toluene mixture (75:95 ml) at stirring. The mixture was settled, the aqueous layer was separated, and organic phase was washed with water and evaporated under vacuum in rotary evaporator. Then 30 ml of absolute ethanol was added to the residue and evaporated.

Addition of ethanol and solvent evaporation under vacuum was repeated.

The residue—16.0 g of oil was mixed with 10 ml absolute ethanol and then added to cold water (0° C., $T_j$=−4° C.) at cooling and stirring. During the addition the batch temperature of 0° C. was maintained.

After the addition completion the dropping funnel was rinsed with 5 ml of absolute ethanol and the rinse was introduced into the reactor. Resulting suspension was stirred at 0° C. for 30 minutes and filtered.

Significant amount of solid product was found deposed on the stirrer and on the reactor surface, poor slurry homogeneity and flowability were also observed. The solid was washed on the filter with 30 ml of water.

Wet solid (16.0 g) was dried at 25° C. and reduced pressure (4-5 mbar) to constant weight. Water content of the dry product was determined by the Karl Fischer (KF) method.

Water content by KF=0.06%.
Dry product=14.1 g, yield=88.2%.

Example 30

Addition of Water to Rasagiline Base Solution in Ethanol, Spiking with AI and PAI Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of absolute ethanol was added to the residue and evaporated.

Addition of ethanol and solvent evaporation under vacuum was repeated.

The residue—16.0 g of oil was mixed with 40 ml absolute ethanol, 1 g racemic PAI base (B.N. 2499800407) and 0.5 g Aminoindan (B.N. 2500300104).

The solvent was distilled out of the resulting solution under vacuum and a 1.5 g sample (Sample 1) was taken from 17.5 g of the residue.

Then the residue (16.0 g) was dissolved in 20 ml absolute ethanol. Water (27 ml) was added to the ethanolic solution for 10 minutes at cooling and stirring. During the addition the batch temperature of 17-18° C. was maintained.

After the addition completion the solution was seeded with solid rasagiline base and crystallization took place. Then additional 11 ml of water was introduced into the reactor. Resulting suspension was cooled, stirred at 1-2° C. for 30 minutes and filtered. The solid was washed on the filter with 30 ml of water.

Wet solid (16.1 g) was dried at ambient temperature under reduced pressure (25 mbar) to constant weight.

Dry product=14.2 g, yield=88.7%.

Example 31

Addition of Water to Rasagiline Base Solution in IPA

Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of IPA was added to the residue and evaporated.

Then the residue (15.9 g) was dissolved in 19.5 ml of IPA. Water (27.2 ml) was added to the solution for 10 minutes at cooling and stirring. During the addition the batch temperature of 14-19° C. was maintained.

After the addition completion the solution was seeded with solid rasagiline base and crystallization took place. Additional 11 ml of water was introduced into the reactor. Resulting suspension was cooled, stirred at 1-2° C. for 30 minutes and filtered. The solid was washed on the filter with 30 ml of water.

Wet solid (15.5 g) was dried at ambient temperature under reduced pressure (25 mbar) to constant weight. Water content of the dry product was determined by the Karl Fischer (KF) method.

Water content by KF=0.20%.
Dry product=14.9 g, yield=93.7%.

Example 32

Addition of Water to Rasagiline Base Solution in Ethanol

Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of ethanol was added to the residue and evaporated.

Then the residue (15.9 g) was dissolved in 19.5 ml of ethanol. Water (27.2 ml) was added to the solution for 10 minutes at cooling and stirring. During the addition the batch temperature of 14-18.5° C. was maintained. The batch was cooled to 12° C. ($T_j$=10° C.) and seeded with solid rasagiline base. Immediate crystallization took place. Then additional 11 ml of water was introduced into the reactor, resulting suspension was cooled, stirred at 1-2° C. for 30 minutes and filtered. The solid was washed on the filter with 30 ml of water.

Wet solid (17.0 g) was dried at ambient temperature under reduced pressure (25 mbar) to constant weight. Water content of the dry product was determined by the Karl Fischer (KF) method.

Water content by KF=0.17%.
Dry product=15.0 g, yield=94.3%.

Example 33

Addition of Water to Rasagiline Base Solution in Ethanol, Spiking with AI and PAI Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of absolute ethanol was added to the residue and evaporated.

Addition of ethanol and solvent evaporation under vacuum was repeated.

The residue—16.0 g of oil was mixed with 40 ml absolute ethanol, 0.5 g racemic PAI base (B.N. 2499800407) and 0.25 g Aminoindan (B.N. 2500300104).

The solvent was distilled out of the resulting solution under vacuum and a 0.75 g sample (Sample 1) was taken from 16.75 g of the residue.

Then the residue (16.0 g) was dissolved in 20 ml absolute ethanol. Water (27 ml) was added to the ethanolic solution for 10 minutes at cooling and stirring. During the addition the batch temperature of 17° C. was maintained.

After the addition completion the solution was seeded with solid rasagiline base and crystallization took place. Then additional 11 ml of water was introduced into the reactor. Resulting suspension was cooled, stirred at 1-2° C. for 30 minutes and filtered. The solid was washed on the filter with 30 ml of water.

Wet solid (16.5 g) was dried at ambient temperature under reduced pressure (25 mbar) to constant weight. Water content of the dry product was determined by the Karl Fischer (KF) method.

Water content by KF=0.21%.
Dry product=14.9 g, yield=93.1%.

Example 34

Addition of Water to Rasagiline Base Solution in Ethanol

Approximately twenty-three grams (20.13 g) of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of ethanol was added to the residue and evaporated.

Then the residue (13.9 g) was dissolved in 19.5 ml of ethanol. Water (27.2 ml) was added to the solution for 10 minutes at cooling and stirring. During the addition the batch temperature of 17° C. was maintained. The batch was seeded with solid rasagiline base and immediate crystallization took place. Then additional 11 ml of water was introduced into the reactor, resulting suspension was cooled, stirred at 1-2° C. for 30 minutes and filtered. The solid was washed on the filter with 30 ml of water.

Wet solid (15.4 g) was dried at ambient temperature under reduced pressure (25 mbar) to constant weight. (Sample 2) Water content of the dry product was determined by the Karl Fischer (KF) method.
  Water content by KF=0.14%.
  Dry product=13.1 g, yield=94.2%.

Example 35

Addition of Water to Rasagiline Base Solution in Ethanol

Twenty-six (26) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of ethanol was added to the residue and evaporated.

Then the residue (17.9 g) was dissolved in 19.5 ml of ethanol. Water (27.2 ml) was added to the solution for 10 minutes at cooling and stirring. During the addition the batch temperature of 19° C. was maintained. The batch was cooled to 13° C. and seeded with solid rasagiline base. Immediate crystallization took place. Then additional 11 ml of water was introduced into the reactor, resulting suspension was cooled, stirred at 1-2° C. for 30 minutes and filtered. Some solid product deposition on the reactor wall was observed. The solid was washed on the filter with 30 ml of water.

Wet solid (19.9 g) was dried at ambient temperature under reduced pressure (25 mbar) to constant weight. Water content of the dry product was determined by the Karl Fischer (KF) method.
  Water content by KF=0.18%.
  Dry product=17.1 g, yield=95.5%.

Example 36

Addition of Water to Rasagiline Base Solution in Ethanol

Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of ethanol was added to the residue and evaporated.

Then the residue (15.9 g) was dissolved in 16 ml of ethanol. Water (27.2 ml) was added to the solution for 10 minutes at cooling and stirring. During the addition the batch temperature of 14-19° C. was maintained. The batch was cooled to 13° C. ($T_j$=10° C.) and seeded with solid rasagiline base. Immediate crystallization took place. Then additional 11 ml of water was introduced into the reactor, resulting suspension was cooled, stirred at 1-2° C. for 30 minutes and filtered. The solid was washed on the filter with 30 ml of water.

Wet solid (17.3 g) was dried at ambient temperature under reduced pressure (25 mbar) to constant weight. Water content of the dry product was determined by the Karl Fischer (KF) method.
  Water content by KF=0.18%.
  Dry product=15.2 g, yield=95.6%.

Example 37

Addition of Water to Rasagiline Base Solution in Ethanol

Twenty-three (23) grams of dry rasagiline tartrate reacted with NaOH (20 g 25% solution) in water-toluene mixture (73:95 ml) at stirring. The mixture was settled, the aqueous layer was separated, and organic phase was washed with water and evaporated under vacuum in rotary evaporator. Then 30 ml of ethanol was added to the residue and evaporated.

Then the residue (16.0 g) was dissolved in 19.5 ml of ethanol. Water (25 ml) was added to the solution for 10 minutes at cooling and stirring. During the addition the batch temperature of 17° C. was maintained. The batch was cooled to 13° C. ($T_j$=10° C.) and seeded with solid rasagiline base. Immediate crystallization took place. Then additional 25 ml of water was introduced into the reactor, resulting suspension was cooled, stirred at 1-2° C. for 30 minutes and filtered. The solid was washed on the filter with 30 ml of water.

Wet solid (19.3 g) was dried at ambient temperature under reduced pressure (25 mbar) to constant weight. Water content of the dry product was determined by the Karl Fischer (KF) method.
  Water content by KF=0.22%.
  Dry product=15.1 g, yield=94.4%.

Summary of Results

The starting material (solid rasagiline base, melt rasagiline base, or racemic PAI), the sublimation conditions, the yield after sublimation, and the mean sublimation rates of examples 1-13 are listed in Table 1 below.

The parameters and conditions for crystallization and drying of rasagiline base, the water content of the dried product, and the percentage yield of the drying process in examples 14-26 are summarized in Table 2.

TABLE 1

Effect of process parameters on PAI sublimation rates

| Experiment GA- | Starting material | | Sublimation conditions | | | Sublimed solid | | Mean sublimation rate | | | |
|---|---|---|---|---|---|---|---|---|---|---|---|
| | Compound | Weight g | Pressure mbar | Temp. ° C. | Time hr | weight mg | fraction %* | $R_{s1}$ g/g/hr | $R_{s2}$ g/hr/m$^2$ | R %/hr | $-\log R_{s1}$ |
| 12 | Solid R-PAI | 4.0 | 2-3 | 21 | 8.0 | 10 | 0.25 | 3.12 10$^{-5}$ | 1.333 | 0.0312 | 4.5 |
| 13 | Solid R-PAI | 3.99 | 2-3 | 35 | 5.33 | 25 | 0.62 | 1.17 10$^{-3}$ | 4.978 | 0.116 | 2.93 |
| 14 | Melt R-PAI | 3.965 | 2-3 | 60 | 4.0 | 890 | 22.4 | 5.62 10$^{-2}$ | 236.19 | 5.6 | 1.25 |
| 15 | Solid R-PAI | 4.0 | 20 | 21 | 8.5 | 0 | 0.0 | 0.0 | 0.0 | 0.0 | — |
| 16 | Solid R-PAI | 4.0 | 40 | 21 | 8.5 | 0 | 0.0 | 0.0 | 0.0 | 0.0 | — |

TABLE 1-continued

Effect of process parameters on PAI sublimation rates

| | Starting material | | Sublimation conditions | | | Sublimed solid | | Mean sublimation rate | | | |
|---|---|---|---|---|---|---|---|---|---|---|---|
| Experiment GA- | Compound | Weight g | Pressure mbar | Temp. °C. | Time hr | weight mg | fraction %* | $R_{s1}$ g/g/hr | $R_{s2}$ g/hr/m² | R %/hr | $-\log R_{s1}$ |
| 17 | Solid R-PAI | 4.0 | 40 | 35 | 5.33 | 8 | 0.20 | $3.75 \cdot 10^{-4}$ | 1.593 | 0.0375 | 3.42 |
| 18 | Solid R-PAI | 3.992 | 20 | 35 | 5.33 | 11 | 0.27 | $5.15 \cdot 10^{-4}$ | 2.192 | 0.0506 | 3.29 |
| 19 | Melt R-PAI | 4.0 | 40 | 60 | 5.33 | 25 | 0.62 | $1.17 \cdot 10^{-3}$ | 4.978 | 0.116 | 2.93 |
| 20 | Melt R-PAI | 3.975 | 20 | 60 | 5.33 | 162 | 4.1 | $7.64 \cdot 10^{-3}$ | 32.26 | 0.769 | 2.12 |
| 21 | Rac.PAI oil | 4.0 | 20 | 22 | 8.0 | 0 | 0.0 | 0.0 | 0.0 | 0.0 | — |
| 22 | Rac.PAI oil | 4.0 | 20 | 35 | 5.33 | 0 | 0.0 | 0.0 | 0.0 | 0.0 | — |
| 23 | Rac.PAI oil | 4.0 | 2-3 | 22 | 3.0 | 10 | 0.25 | $8.33 \cdot 10^{-4}$ | 3.537 | 0.08 | 3.08 |
| 24 | Rac.PAI oil | 4.0 | 2-3 | 60 | 1.3 | 130 | 3.25 | $2.50 \cdot 10^{-2}$ | 101.16 | 2.5 | 1.60 |

TABLE 2

Crystallization and drying process parameters

| | Solvent | | | Crystallization | Drying | Drying | Water | |
|---|---|---|---|---|---|---|---|---|
| Experiment No. | Type | Ratio, ml/g base | Water ratio, ml/g base | temperature, °C. | conditions mbar | conditions °C. | content by KF (%) | Dry product yield % |
| 25 | EtOH | 1.27 | 2.46 | 18-20 | 4-5 | 25 | 0.18 | 90.9 |
| 26 | IPA | 1.27 | 2.46 | 18-20 | 4-5 | 25 | 0.21 | 92.5 |
| 27 | IPA | 1.25 | 1.69 | 0-5 | 4-5 | 25 | 0.06 | 86.7 |
| 28 | No | 0 | 3.75 | 0-5 | 4-5 | 25 | 0.10 | 88.2 |
| 29 | EtOH | 1.25 | 3.75 | 0 | 4-5 | 25 | 0.06 | 88.2 |
| 30 | EtOH | 1.25 | 2.38 | 17-18 | 25 | RT | N/A | 88.7 |
| 31 | IPA | 1.23 | 2.40 | 14-19 | 25 | RT | 0.20 | 93.7 |
| 32 | EtOH | 1.23 | 2.40 | 17-18.5 | 25 | RT | 0.17 | 94.3 |
| 33 | EtOH | 1.25 | 2.40 | 17 | 25 | RT | 0.21[1] | 93.1 |
| 34 | EtOH | 1.40 | 2.75 | 17 | 25 | RT | 0.14 | 94.2 |
| 35 | EtOH | 1.09 | 2.13 | 17 | 25 | RT | 0.18 | 95.5 |
| 36 | EtOH | 1.00 | 2.40 | 17 | 25 | RT | 0.18 | 95.6 |
| 37 | EtOH | 1.22 | 3.12 | 17-18.5 | 25 | RT | 0.22 | 94.4 |

[1]Sample 2 only

Discussion

The data show that rasagiline base and racemic PAI base have similar sublimation ability, i.e., the sublimation rates of the R-isomer and racemic mixture are similar.

Figure 2:
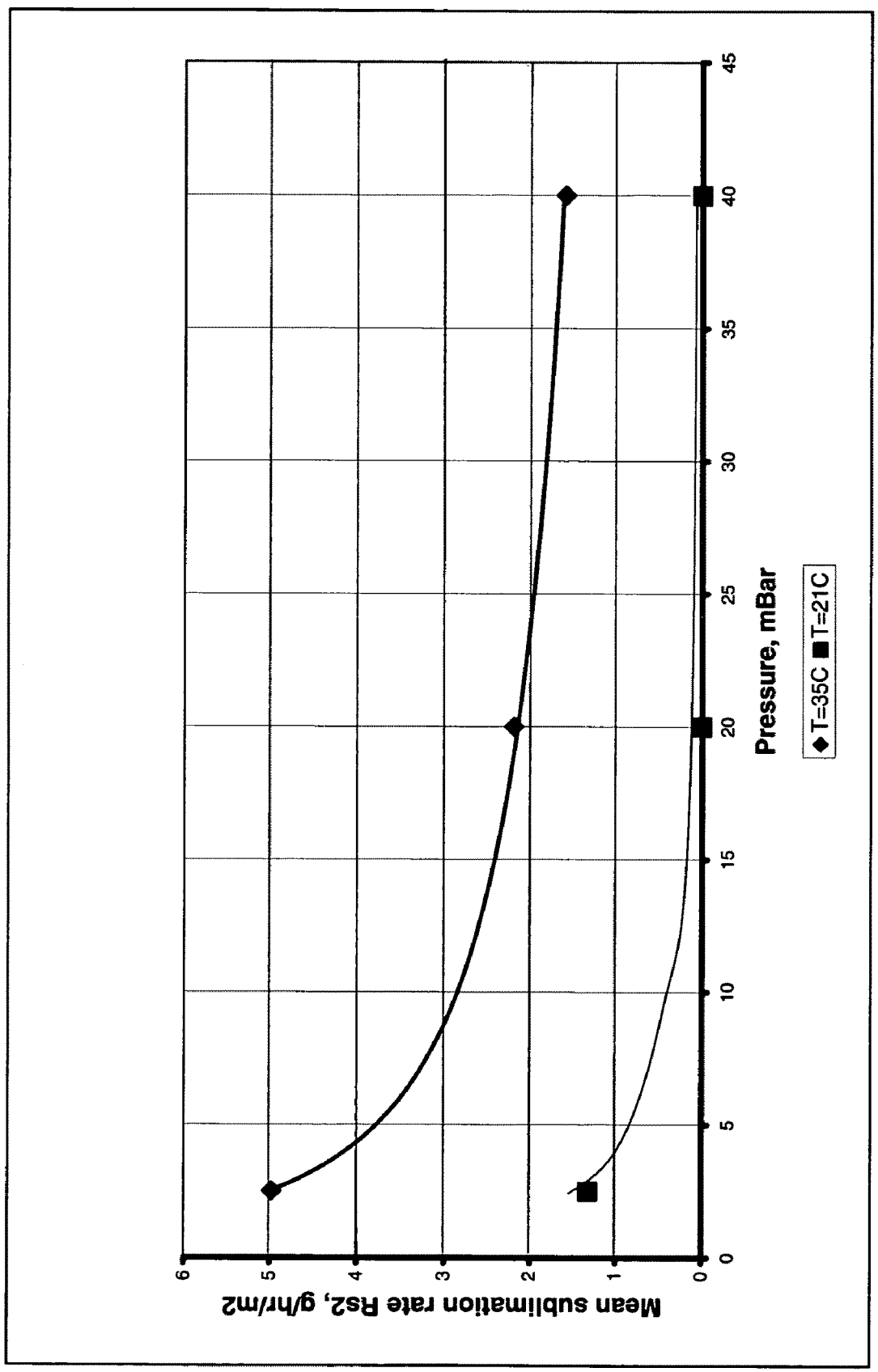
FIG. 2 shows the effect of pressure and temperature on solid rasagiline base sublimation rate.

Effects of vacuum and temperature on sublimation rate of rasagiline base and racemic PAI base are represented graphically on FIG. 1 and FIG. 2.

The figures demonstrate that at high vacuum (pressure less than 3 mbar) and elevated temperatures (60° C. and higher), high sublimation rate was observed.

The figures also demonstrate that at moderate vacuum (pressure higher than 20 mbar) and low temperatures (less than 22° C.), zero sublimation rate was observed.

The figures further demonstrate that at a temperature of between 0° C. and 20° C. and a pressure of between 4-25 mbar, dried rasagiline contains between 0.06-0.22% water by weight, and the dry product yield is between 86.7%-95.6% by weight.

Conclusions

Moderate vacuum (pressure higher than 20 mbar) and low temperatures (less than 35° C.) could be recommended as conditions for drying of solid rasagiline base from solvent after crystallization.

Experimental Details

Set 3: Drying and Purifying of Rasagiline Base

Wet Rasagiline Tartrate was used for the production of Rasagiline base which contained 27.8% of isopropanol.

1. The Production Process

A number of processes for manufacture of rasagiline solid base are described in PCT International Application Publication No. WO 2008/076348, the content of which is hereby incorporated by reference. One batch was manufactured according to the production process described.

1.1. The Process

Example 38

Preparation of Rasagiline Base Solid—Large Scale

The production process included the following operations:
a. Splitting of wet Rasagiline Tartrate with NaOH:

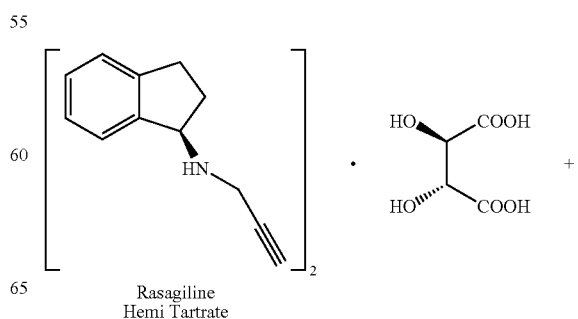

Rasagiline Hemi Tartrate

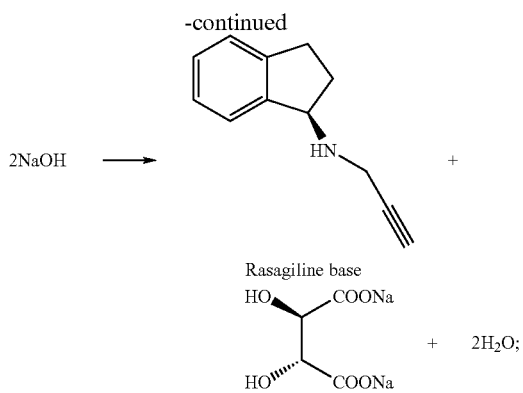

b. Isolation of free Rasagiline base as oil-like product;
c. Dissolution of Rasagiline base in Ethanol and seeding induced crystallization of the Rasagiline base by water addition;
d. Filtration and wash of the solid product; and
e. Drying of the solid Rasagiline base.

Since Rasagiline base is low melting material it is processed in to the Drug Product without milling.

Process parameters and conditions are summarized in Tables 1.1-1.3 below.

TABLE 1.1

Process parameters for Rasagiline base production - Tartrate splitting and Rasagiline base isolation steps

| Process parameters: | | Unit | Amount |
|---|---|---|---|
| Amount of Rasagiline Tartrate (starting material) | | | |
| Wet | | kg | 9.5 |
| Dry | | kg | 6.86 |
| Total amount of 25% NaOH solution | | kg | 7.0 |
| pH after basification | | | 13 |
| Reactor temperature during the basification and splitting | | ° C. | 41-47 |
| Duration of the basification, splitting and wash | | hrs | 3.5 |
| Toluene evaporation | Duration | hrs | 3.3 |
| | End of evaporation temperature | ° C. | 60 |
| | End of evaporation pressure | mmHg | 38 |
| Ethanol evaporation | Duration | hrs | 1.6 |
| | End of evaporation temperature | ° C. | 60 |
| | End of evaporation pressure | mmHg | 44 |
| Rasagiline base oil dissolution | Duration | min | 27 |
| | Reactor temperature (T$_r$) | ° C. | 30-40 |
| Filtration (0.2µ) and wash | Duration | min | 4 + 1 |
| | Solution temperature | ° C. | 35-40 |

TABLE 1.2

Process parameters or Rasagiline base production - Rasagiline base crystallization steps

| Process parameters: | | Unit | Amount |
|---|---|---|---|
| Ethanolic solution holding | Duration | hrs | 7.7 |
| | Solution temperature* | ° C. | 10-22 |
| Amount of water introduced prior to seeding | | kg | 2.3 |
| | | %** | 19.2 |
| Seeding and breeding | Temperature, (T$_r$) | ° C. | 14 |
| | Stirrer speed | rpm | 112 |
| | Duration | hrs | 2 |

TABLE 1.2-continued

Process parameters or Rasagiline base production - Rasagiline base crystallization steps

| Process parameters: | | Unit | Amount |
|---|---|---|---|
| Water addition | Temperature, (T$_r$) | ° C. | 11-12 |
| | Duration | min | 66 |
| Cooling | End temperature, (T$_r$) | ° C. | 4 |
| | Stirrer speed | rpm | 112-177 |
| | Duration | min | 95 |
| Batch stirring prior to filtration | Duration | min | 36 |
| | Temperature, (T$_r$) | ° C. | 3-4 |

**percent on total volume of added water

TABLE 1.3

Process parameters for Solid Rasagiline base isolation - filtration, washing, drying

| Process parameters: | | Unit | Amount |
|---|---|---|---|
| Filtration and cake purging time | | Min. | 7 |
| Washing time (two washes) | | Min. | 1 + 1 |
| Drying | Pressure | mmHg | 23-30 |
| | Temperature (T$_j$) | ° C. | 23-35 |
| | Agitator speed | rpm | 8 |
| | Duration (agitated) | hrs | 48 (34) |
| Water in dry product by K.F. | | % | 0.05 |
| Dry product yield, % calculated on dry starting Rasagiline Tartrate | | kg | 3.7 |
| | | % | 77.7 |

1.2. Results and Discussion

During the production of the batch, there were two technical problems related to large scale processing—spontaneous crystallization of Rasagiline base oil and ineffective drying of solid product.

In addition to the above mentioned two issues, the content of S-isomer in the drug substance was 0.35%, which is much higher than the specification level (NMT. 0.1%).

These three issues are discussed below in details.

1.2.1. Crystallization and Dissolution of Rasagiline Base Oil

Isolated Rasagiline base oil between the operations step 1.2 and 1.3 was stored in the reactor under nitrogen at cooling overnight. The base solidified forming a block in the bottom part of the reactor. The solid glass like mass of Rasagiline base was dissolved in absolute ethanol in more than 2 hours.

The proposed solution of this problem was to prevent the solidification of Rasagiline base oil by holding its solution in ethanol between the operations 2 and 3. Laboratory simulation experiments were performed in order to evaluate the effect of this process change on yield and purity of crystallized product.

1.2.1.1. Laboratory Scale Simulation

Two batches of Rasagiline base were prepared in order to simulate the storage of Rasagiline base in ethanol solution at different temperatures.

The experiments and the results are detailed below:

Example 39

Rasagiline Base Oil Hold in Ethanol Solution for 48 hrs at Cooling (7-8° C.)

17.0 g of Rasagiline base oil was dissolved in 17 g absolute ethanol. The resulting solution was introduced into refrigerator and stored at 7-8° C. for 48 hrs. The ethanol solution was sampled. (sample 1).

The clear solution was then introduced into 100 ml jacketed glass reactor equipped with a stirrer, thermometer and circulating oil bath.

The reactor was cooled ($T_j=11°$ C.) and 8 g of water was introduced at stirring. Then the solution was seeded with solid Rasagiline base and crystallization was observed. The batch was stirred for 15 min at 11-12° C. and then 33.8 g of water was added. The resulting suspension was cooled to 4° C. and stirred at 1-4° C. for 30 min. The solid was filtered and washed twice with 17 ml water. Wet solid product (17.6 g) was dried under vacuum.

Dry product—15.7 g
Crystallization yield—92%
Analysis:
Sample 1 (Solution):
  Purity by HPLC:
    S-isomer—0.77%
    IDD—1-Aminoindan—L.T. 0.05% (QL)
Dry Product:
  Color—White to off-white
  Assay—99.5%
  IDD—N.D.
  S-isomer—0.01%
  m.p.—39.5-40.4° C.
  Water content by K.F.—0.2% wt.

Example 40

Rasagiline Base Oil Hold in Ethanol Solution for 48 hrs at Ambient Temperature 17.0 g of Rasagiline base oil was dissolved in 17 g absolute ethanol. The resulting solution was stored at ambient temperature (20-28° C.) for 48 hrs. The ethanol solution was sampled (sample 1).

The clear solution was then introduced into 100 ml jacketed glass reactor equipped with stirrer, thermometer and circulating oil bath.

The reactor was cooled ($T_j=11°$ C.) and 8 g of water was introduced at stirring. Then the solution was seeded with solid Rasagiline base and crystallization was observed. The batch was stirred for 20 min at 11-12° C. and then 33.8 g water was added. The resulting suspension was cooled to 4° C. and stirred at 1-4° C. for 30 min. The batch was filtered and washed twice with 17 ml water. Wet solid product (18.2 g) was dried under vacuum.

Dry product—15.9 g
Crystallization yield—93.5%
Analysis:
Sample 1 (Solution):
  Color—Yellowish
  Purity by HPLC:
    S-isomer—0.76%
    IDD—1-Aminoindan—L.T. 0.05% (QL)
Dry Product:
  Assay—99.9%
  IDD—N.D.
  S-isomer—0.01%
  Melting range—39.6-40.6° C.
  Water content by K.F.—0.1% wt.

1.2.1.2. Results, Discussion and Conclusion

The data presented above demonstrate that holding of Rasagiline base as ethanol solution for 48 hrs in air prior to crystallization do not affect the yield and quality of solid product. Crystalline Rasagiline base prepared from the solution stored at low temperature (7-8° C.) has the same purity as the product prepared from the solution stored at room temperature.

As a result, rasagiline base between the isolation and crystallization operation should be held in ethanol solution. This operation mode prevents spontaneous crystallization of Rasagiline base oil and problems with its dissolution.

1.2.2. Drying

Wet Rasagiline base was dried under vacuum (23-30 mm Hg) at ambient temperature (23° C.) with no stirring for 14 hours with any results. The solid remained wet and contained 28% water.

After 14 hours of static drying the cake was stirred (8 rpm) and the dryer jacket was gradually heated to 35° C. during 9 hours. At this step the drying rate was increased significantly—the cake was sampled and only 15% of water was found in the solid.

The drying was continued under the same conditions for additional 17 hours (overnight). Then the cake was sampled and found dry (0.07% of water).

Additional 8 hours of drying had no significant effect on water content—0.05% of water was found in the next sample.

The drying regime mentioned above (P<35 mm Hg; $T_j=35°$ C. and stirring 8 rpm) was found effective for Rasagiline base.

1.2.3. Solid Uniformity

In the above drying process, the Drug Substance (DS) is homogenized by prolonged stirring during the drying operation. A special sampling program was prepared and performed during the production in order to prove the homogeneity and uniformity of the DS after the drying.

Dry Rasagiline base was sampled 5 times from different zones of the dryer. Additional 6$^{th}$ sample was prepared by mixing of the materials from each of the 5 sample. These six samples were analyzed for water content, assay, purity, melting point, s-isomer content and particle size distribution. The results of analysis are shown in Table 2.1. The data show uniformity of the dry product.

TABLE 2.1

Rasagiline base samples analysis results

| | Sample: | | | | | |
|---|---|---|---|---|---|---|
| | 01-1 | 01-2 | 01-3 | 01-4 | 01-5 | Mix |
| | | | Color | | | |
| | Off-white | Off-white | Off-white | Off-white | Off-white | Off-white |
| S-isomer, % | 0.36 | 0.36 | 0.32 | 0.35 | 0.35 | >0.1 (OOS) |
| IDD, (%) | N.D. (>0.02) | N.D. (>0.02) | N.D. (>0.02) | N.D. (>0.02) | N.D. (>0.02) | N.D. (>0.02) |
| Assay by HPLC, % | 99.9 | 100.7 | 99.7 | 99.9 | 100.1 | 99.0 |
| Water by K.F., % | 0.05 | 0.04 | 0.05 | 0.05 | 0.04 | 0.04 |

TABLE 2.1-continued

Rasagiline base samples analysis results

| | \multicolumn{6}{c}{Sample:} | | | | | |
|---|---|---|---|---|---|---|
| | 01-1 | 01-2 | 01-3 | 01-4 | 01-5 | Mix |
| | \multicolumn{6}{c}{Color} | | | | | |
| | Off-white | Off-white | Off-white | Off-white | Off-white | Off-white |
| Melting range, °C. | 38.7-39.7 | 38.8-40.0 | 38.8-39.4 | 38.8-39.5 | 38.8-39.8 | N.A. |
| PSD by Malvern, Microns | | | | | | |
| d(0.1) | 242.5 | 236.8 | 249.8 | 239.9 | 249.3 | 235.3 |
| d(0.5) | 549.0 | 539.4 | 562.1 | 543.3 | 557.6 | 531.6 |
| d(0.9) | 1124.4 | 1121.1 | 1148.8 | 1111.3 | 1117.2 | 1076.7 |
| Morphology group | 1 | 1 | 1 | 1 | 1 | 1 |

The data in the above table demonstrate that the dryer provides effective homogenization of 3.5 kg batch of Rasagiline base.

1.2.4. S-Isomer in Solid Product

The data presented in Table 2.1 demonstrate high level of S-isomer (OOS) found in the batch of Rasagiline base.

The data were found surprising because the typical S-isomer level in the crystalline base was below 0.1%. In small scale rasagiline base prepared contained 0.02-0.03% of this impurity. The level of 0.35% of S-isomer in the crystallization product could be obtained using a starting material having more than 2% of this impurity.

1.2.4.1. Simulation of the Crystallization

Figure 3:
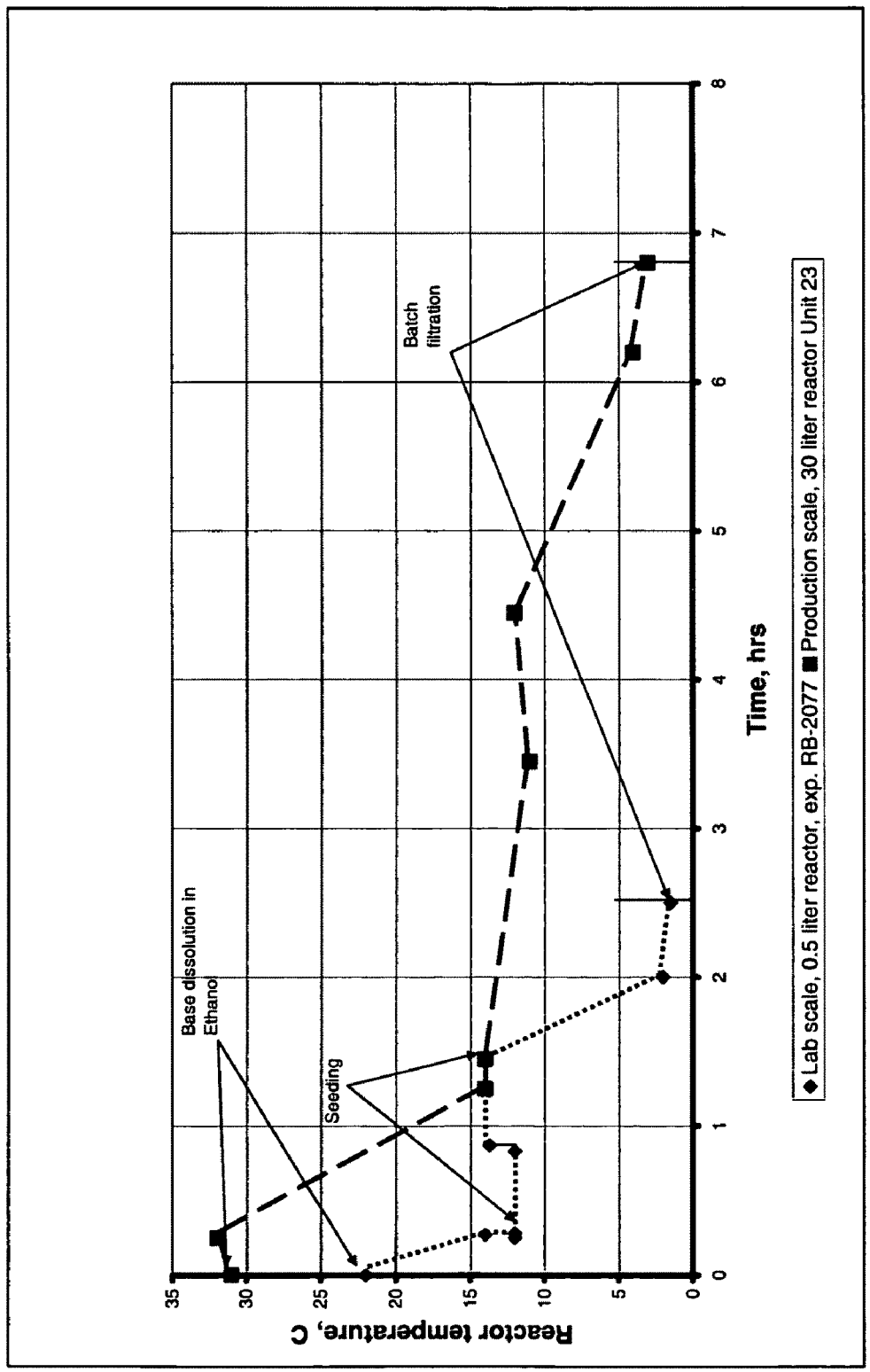
FIG. 3 compares the temperature profiles of Rasagiline base preparation on small and large scales.

The difference in processing time is illustrated by comparison of temperature profiles of pilot and laboratory batches on FIG. 3.

Crystallization of small scale normally takes about 2.5 hours, but the large scale was processed during 6.5 hours. The effect of processing time on optical purification was studied in the following experiments.

Example 41

Rasagiline Base Preparation 100 g of wet Rasagiline Tartrate was mixed with 160 ml water at stirring. 63 g of 25% NaOH solution and 200 g toluene were added to the mixture, the batch was stirred for 1 hour at 40-50° C. (pH=13) and then settled at this temperature for 0.5 hour. Lower aqueous phase was separated and discarded and 100 ml of water was added to the batch. Then the mixture was stirred for 0.5 hour and settled for 0.5 hour at 40-50°. Lower aqueous phase was separated and discarded. Upper organic phase was evaporated on rotary evaporator under vacuum. Temperature profile of the evaporation was the same as in the pilot batch—total evaporation time was 3 hrs 20 min, the residue was exposed to temperature 55° C. during 1 hr 20 min and to 60° C. during 2 hrs.

After evaporation of toluene 75 g of absolute ethanol was added to the residue and the evaporation was continued. Total evaporation time was 2 hrs 40 min, the residue was exposed during the evaporation to temperature 55° C. and then to 60° C.

Residual product—oil of Rasagiline base (52 g) was cooled and stored at 5° C. overnight. Then the base was dissolved in 52 g of absolute ethanol at stirring and 24 ml of water was added. Then the resulting clear solution was cooled to 12.5° C. and seeded with crystalline Rasagiline base. The crystallizing batch was stirred at 11-12° C. for 2 hours. 103 g of water was introduced dropwise during one hour at cooling then the batch was cooled to 4° C. during 1 hour 45 min and stirred at 1-4° C. for 30 min.

One half of the batch was withdrawn out of crystallizer and filtered. The solid was washed with 50 ml of water and dried under vacuum. Dry product (26.2 g) and filtrate (mother liquor) were sampled—Samples 4 (solid) and 2 (M.L.)

The second half of the batch was stirred at cooling (1° C.) overnight, total holding time at T<4° C. was 14 hrs. Then this half batch was filtered, the solid was washed with 50 ml water and dried under vacuum. Dry product (17.8 g) and filtrate (mother liquor) were sampled—Samples 7 (solid) and 5 (M.L.)

Analysis:
Solids:
Sample 4:
  S-isomer—N.D.
  Assay by HPLC—99.4%
  Purity by HPLC (IDD)—N.D.
  Melting range—39.8-40.5° C.
Sample 7:
  S-isomer—N.D.
  Assay by HPLC—99.5%
  Purity by HPLC (IDD)—N.D.
  Melting range—39.5-40.7° C.
Mother Liquors:
Sample 2:
  S-isomer—31.3%
  Rasagiline concentration by HPLC—5.8 mg/ml
  Purity by HPLC (IDD)—1-Aminoindan—1.37%; RRT=1.47—0.03%; RRT=1.60—0.05%; 1-Indanone—0.15%, RRT=7.8—0.07%
Sample 5:
  S-isomer—26.9%
  Rasagiline concentration by HPLC—6.8 mg/ml
  Purity by HPLC (IDD)—1-Aminoindan—1.17%; RRT=1.47—0.03%; RRT=1.60—0.04%; 1-Indanone—0.13%

1.2.4.2. Results, Discussion and Conclusion

Level of S-isomer in Rasagiline base prepared using prolonged crystallization (14 hours, Sample 7) was undetectable. The same level of this impurity was found in the product crystallized during 1 hour (Sample 4).

In Table 3.1 composition of mother liquors of the small scale experiments is compared to the mother liquor of a large batch. Table 3.1 shows that purity profiles of the mother liquor in the simulation experiments are very similar to the large scale batch. At the same time concentration of S-isomer in large scale mother liquor is about 3 times lower than in the small scale experiments.

TABLE 3.1

Composition of laboratory and pilot mother liquors of Rasagiline base crystallization

|  |  | Example No. 41 - Sample 5 | Example No. 41 - Sample 2 | Example No. 38 |
|---|---|---|---|---|
| Holding at T < 4° C. | hrs | 14 | 1 | 1 |
| S - isomer | % | 26.9 | 31.3 | 9.7 |
| Rasagiline base conc. | mg/ml | 6.8 | 5.8 | 7.9 |
| IDD: |  |  |  |  |
| RRT = 0.45 | % area | N.D. | 0.02 | N.D. |
| 1-AI |  | 1.17 | 1.37 | 0.93 |
| RRT = 1.5 |  | 0.03 | 0.03 | N.D. |
| RRT = 1.6 |  | 0.04 | 0.05 | 0.05 |
| 1-Indanone |  | 0.13 | 0.15 | 0.02 |
| RRT = 7.8 |  | N.D. | 0.07 | 2.06 |

The data show that the racemization of R-isomer of Rasagiline base does not take place under the large scale process conditions. The results of simulation experiment show that processing time has no effect on optical purification of Rasagiline base.

Two possible solutions for the S-isomer problem:
i) Re-crystallization of S-isomer contaminated Rasagiline base; and
ii) Additional optical purification of starting material—Rasagiline Tartrate.

These two approaches were studied on both small scale and large scale for the production of Rasagiline base Drug Substance. The study is described in the following sections.
2. Optical Purification of Rasagiline Base
2.1. Re-Crystallization of Rasagiline Base—Small Scale Rasagiline base with 0.35% of S-isomer from the rejected pilot batch 255500208 was re-crystallized in the laboratory using the same crystallization procedure as was used on pilot scale.

Example 42

Rasagiline Base Re-Crystallization 49.5 g of Rasagiline base introduced into 0.5 liter jacketed glass reactor with 52 g of absolute ethanol. The batch was stirred and heated ($T_j$=35° C.) until complete dissolution of the solid.

The solution was cooled and 24 g of water was added at stirring. The resulting clear solution was seeded at 12° C. with solid Rasagiline base and stirred at 11-12° C. for one hour. Crystallization was observed on this step.

103 g of water was added at cooling and stirring during 20 minutes then the batch was cooled to 4° C. and stirred at 2-4° C. for 45 minutes.

The batch was cooled, the solid washed with 2×50 ml water and dried under vacuum to constant weight.

The solid product (45.5 g) was sampled (Sample 1)

Filtrate (combined Mother Liquor and washes) was evaporated under vacuum in rotary evaporator. The oily evaporation residue (1.1 g) was sampled (Sample 2) and subjected to analysis with the solid product.

Analysis:
Solid:
Sample 1:
 S-isomer—N.D.
 Assay by HPLC—98.8%
 Purity by HPLC (IDD)—3PAIO—L.T. 0.05% (QL); 1-Aminoindan—L.T. 0.05% (QL); 1-Indanone—L.T. 0.05% (QL) Melting range—39.1-39.8° C.
Mother Liquor:
Sample 2 (Residue after Evaporation):
 Assay by HPLC—91.3%
 S-isomer—7.8%
 Purity by HPLC (IDD)—3PAIO—L.T. 0.05% (QL); 1-Aminoindan—0.2%; RRT=0.92–0.08%; RRT=1.62–0.13%; RRT=2.27–0.05%; 1-Indanone—L.T. 0.05% (QL); RRT=6.6–0.1%; Total IDD—0.5%
2.2. Discussion and Conclusions The experiment detailed above demonstrates the possibility of complete separation of S-isomer from Rasagiline base having 0.35% of this impurity. This result is in accordance with our previous findings of optical purification on laboratory scale.
3. Purification of Rasagiline Tartrate
3.1. General Considerations Crystallization of Rasagiline salts as Rasagiline Tartrate could result in complete separation of S-isomer from the Tartrate. Purified Rasagiline Tartrate with very low level of S-isomer could be converted into Rasagiline base with almost zero content of this impurity with effect on the optical purity in a large scale batch.

Study of Rasagiline Tartrate re-crystallization was performed in order to evaluate the possibility of additional optical purification of this intermediate.
3.2. Re-Crystallization of Rasagiline Tartrate
3.2.1. Procedure Evaluation Rasagiline Tartrate crystallization experiments were performed in 0.5 liter jacketed glass reactors equipped with stirrer, circulating oil bath for heating and cooling, condenser and thermometer. Vacuum oven was used for solid drying.

Starting material with 0.7% of S-isomer was used in all experiments. Solid and liquid products were analyzed for IDD and S-isomer by HPLC.

Example 43

Crystallization from 8 Volumes of Water 50.0 g of Rasagiline Tartrate was introduced into reactor, 300 ml of water was added, the mixture was stirred and heated ($T_j$=85° C.), at 72° C. complete dissolution of solids was observed.

The reactor was cooled slowly and seeded with Rasagiline Tartrate at 63° C. Then crystallization was observed and the reactor was cooled to 20° C. during 2 hrs. After stirring for 30 min at 20° C. the batch was filtered, the solid washed with 30 ml water and dried under vacuum at 50° C. to constant mass.
 Wet solid—36.9 g
 Dry solid—26.6 g
 Yield—70.9%
Analysis:
Solid:
 Appearance—White solid
 S-isomer—0.01% area
 1-Aminoindan<0.08% by HPLC against analytical standard IDD—no additional peaks detected Mother Liquor:
S-isomer—2.48% area
1-Aminoindan—0.26% area, IDD—RRT=1.96–0.01% area; RRT=2.29–0.02% area against the main peak of Rasagiline Example 44

Slurry-to-Slurry Re-Crystallization from 4 Volumes of Water 50.0 g of Rasagiline Tartrate was introduced into reactor with 150 ml of water, the mixture was stirred and heated ($T_j$=85° C.), to 75° C., no dissolution of solids was observed.
The resulting slurry was stirred at 75° C. for 90 minutes and cooled to 12° C. during 40 min. After stirring for 40 min at 10-12° C. the batch was filtered, the solid washed with 40 ml water and dried under vacuum at 50° C. to constant mass.
Wet solid—38.4 g
Dry solid—26.7 g
Yield—71.1%
Analysis:
Solid:
Appearance—White solid
S-isomer—0.11% area
1-Aminoindan<0.08% by HPLC against analytical standard IDD—no additional peaks detected
Mother Liquor:
S-isomer—2.62% area
1-Aminoindan—0.35% area, IDD—RRT=1.96–0.02% area—against the main peak of Rasagiline Example 45

Slurry-to-Slurry Re-Crystallization from 4 Volumes of Water, Crop B Precipitation with Anti-Solvent Crop A:
50.0 g of Rasagiline Tartrate was introduced into reactor with 150 ml of pre-heated water ($T_j$=85° C.), the mixture was stirred and heated, to 75° C., no dissolution of solids was observed. The resulting slurry was stirred at 75-77° C. for 90 minutes and cooled to 7° C. during one hour. After stirring for 40 min at 5-7° C. the batch was filtered, the solid washed with 75 ml water and dried under vacuum at 50° C. to constant mass.
Wet solid—40.5 g
Dry solid—30.7 g
Yield—81.9%
Analysis:
Solid:
Appearance—White solid
S-isomer—0.11% area
1-Aminoindan<0.08% by HPLC against analytical standard IDD—no additional peaks detected
Mother Liquor:
S-isomer—4.47%
1-Aminoindan—0.62% area; IDD—RRT=1.96–0.06% area—against the main peak of Rasagiline
Crop B:
Mother Liquor from Crop A filtration divided on two equal portions (70 ml each)
1$^{st}$ Portion, Precipitation with Isopropanol
Mother Liquor cooled to 7° C. at stirring, 20 ml IPA was added, solid precipitation observed. The suspension was stirred at 5-7° C. for 30 min and filtered. The solid washed with IPA and dried under vacuum at 50° C. to constant mass.
Wet solid—0.9 g
Dry solid—0.7 g
Yield—1.9%
Analysis:
Solid:
Appearance—White solid
S-isomer—0.15% area
1-Aminoindan<0.08% by HPLC against analytical standard IDD—no additional peaks detected
Mother Liquor:
S-isomer—8.36% area
1-Aminoindan—1.14% area; IDD—RRT=0.37–0.02% area; RRT=0.79–0.01% area; RRT=1.32–0.01% area; RRT=1.40–0.02% area; RRT=1.88–0.03% area; RRT=1.96–0.11% area—against the main peak of Rasagiline
2$^{nd}$ Portion, Precipitation with Ethanol
Mother Liquor cooled to 7° C. at stirring, 20 ml Ethanol was added, solid precipitation observed. The suspension was stirred at 5-7° C. for 30 min and filtered. The solid washed with Ethanol and dried under vacuum at 50° C. to constant mass.
Wet solid—0.9 g
Dry solid—0.6 g
Yield—1.6%
Analysis:
Solid:
Appearance—White solid
S-isomer—0.07% area
1-Aminoindan<0.08% by HPLC against analytical standard IDD—no additional peaks detected
Mother Liquor:
S-isomer—6.76% area
1-Aminoindan—0.93% area; IDD—RRT=0.37–0.01% area; RRT=0.79–0.02% area; RRT=1.32–0.01% area; RRT=1.96–0.08% area—against the main peak of Rasagiline Example 46

Slurry-to-Slurry Re-Crystallization from 4 Volumes of Water and Isopropanol 50.0 g of Rasagiline Tartrate was introduced into reactor with 150 ml of water. The mixture was stirred and heated ($T_j$=85° C.), to 75° C., no dissolution of solids was observed. The resulting slurry was stirred at 77-79° C. for 90 minutes and then cooled to 25° C. 40 ml of IPA was added and the batch was cooled to 5° C. After stirring for 30 min at 5° C. the batch was filtered, the solid washed with 30 ml IPA and dried under vacuum at 50° C. to constant mass.
Wet solid—47.9 g
Dry solid—35.9 g
Yield—95.7%
Analysis:
Solid:
Appearance—White solid
S-isomer—0.07% area
1-Aminoindan<0.08% by HPLC against analytical standard IDD—no additional peaks detected

TABLE 4.1

Rasagiline Tartrate re-crystallization

| | | Example No.: | | | |
|---|---|---|---|---|---|
| | | 43 | 44 | 45 (crop A) | 46 |
| Purification procedure | | Crystallization from solution | Slurry to slurry | Slurry to slurry | Slurry to slurry |
| Water to Tartrate ratio (on dry basis) | g/g | 8 | 4 | 4 | 4 |
| Anti-solvent (ratio to water) | ml/ml | — | — | — | IPA (0.27) |
| Cooling temperature | ° C. | 20 | 12 | 7 | 5 |
| Washing | ml/g dry solid | Water 1.1 | Water 1.5 | Water 2.4 | IPA 0.8 |
| Pure Tartrate yield (on dry basis) | % | 70.9 | 71.1 | 81.9 | 95.7 |
| S-isomer content: | | | | | |
| In Tartrate | % | 0.01 | 0.11 | 0.11 | 0.07 |
| In Mother Liquor | area | 2.48 | 2.62 | 4.47 | N.A. |
| 1-Aminoindan content: | | | | | |
| In Tartrate | % wt. | L.T. 0.08 | L.T. 0.08 | L.T. 0.08 | N.A. |
| In mother liquor | % area | 0.26 | 0.35 | 0.62 | N.A |

The results in the above Table 4.1 show that re-crystallization of Rasagiline Tartrate from 4 volumes of water in slurry-to-slurry regime is very effective providing good yield and high optical purity. Additional work was performed in order to optimize the method and to evaluate the effect of process parameters on Rasagiline Tartrate purification.

3.2.2. Process Parameterization

The following examples were performed to study the effect of most important process parameters on yield and purity of re-crystallized Rasagiline Tartrate.

Example 47

Slurry-to-Slurry Re-Crystallization from 4 Volumes of Water and Isopropanol, $T_j=100°$ C.

50.0 g of Rasagiline Tartrate was introduced into reactor with 150 ml of water. The mixture was stirred and heated ($T_j=100°$ C.), to 90° C., dissolution of most of the solid was observed. The resulting slurry was stirred at 90° C. for 90 minutes and then cooled to 25° C. 40 ml of IPA was added and the batch was cooled to 5° C. After stirring for 30 min at 5° C. the batch was filtered, the solid washed with 30 ml IPA and dried under vacuum at 50° C. to constant mass.
  Wet solid—57.7 g
  Dry solid—37.9 g
  Yield—93.7% (calculated according to starting material L.O.D.=20%)
Analysis:
Solid:
  Appearance—White solid
  S-isomer—0.01% area
  IDD—no additional peaks detected
  1-Aminoindan—N.D.

Example 48

Slurry-to-Slurry Re-Crystallization from 4 Volumes of Water and Isopropanol, $T_j=65°$ C.

50.0 g of Rasagiline Tartrate was introduced into reactor with 150 ml of water. The mixture was stirred and heated ($T_j=65°$ C.), to 63° C., no dissolution of solids was observed. The resulting slurry was stirred at 63-64° C. for 90 minutes and then cooled to 25° C. 40 ml of IPA was added and the batch was cooled to 5° C. After stirring for 30 min at 5° C. the batch was filtered, the solid washed with 30 ml IPA and dried under vacuum at 50° C. to constant mass.
  Wet solid—55.0 g
  Dry solid—37.7 g
  Yield—94.5%
Analysis:
Solid:
  Appearance—white solid
  S-isomer—0.32% area
  1-Aminoindan<0.08% by HPLC against analytical standard IDD—no additional peaks detected Example 49

Slurry-to-Slurry Re-Crystallization from 4 Volumes of Water and Isopropanol, $T_j=85°$ C., Stirring Time—15 min 50.0 g of Rasagiline Tartrate was introduced into reactor with 150 ml of water. The mixture was stirred and heated ($T_j=85°$ C.), to 75° C., dissolution of most of the solid was observed. The resulting slurry was stirred at 75° C. for 15 minutes and then cooled to 25° C. 40 ml of IPA was added and the batch was cooled to 5° C. After stirring for 30 min at 5° C. the batch was filtered, the solid washed with 30 ml IPA and dried under vacuum at 50° C. to constant mass.
  Wet solid—55.0 g
  Dry solid—37.5 g
  Yield—93.7% (calculated according to starting material L.O.D.=20%)
Analysis:
Solid:
  Appearance—White solid
  S-isomer—0.19% area
  IDD—no additional peaks detected
  1-Aminoindan—N.D.

Example 50

Slurry-to-Slurry Re-Crystallization from 4 Volumes of Water and Isopropanol, $T_j=85°$ C., Stirring Time—150 min 50.0 g of Rasagiline Tartrate was introduced into reactor with 150 ml of water. The mixture was stirred and heated ($T_j=85°$ C.), to 75° C., dissolution of most of the solid was observed. The resulting slurry was stirred at 75° C. for 150 minutes and then cooled to 25° C. 40 ml of IPA was added and the batch was cooled to 5° C. After stirring for 30 min at 5° C. the batch was filtered, the solid washed with 30 ml IPA and dried under vacuum at 50° C. to constant mass.
  Wet solid—51.9 g
  Dry solid—38.4 g
  Yield—96.0% (calculated according to starting material L.O.D.=20%)

Analysis:
Solid:
  Appearance—White solid
  S-isomer—0.10% area
  IDD—no additional peaks detected
  1-Aminoindan—N.D.

Example 51

Slurry-to-Slurry Re-Crystallization from 4 Volumes of Water and Isopropanol, $T_j$=85° C., 100 ml of IPA 50.0 g of Rasagiline Tartrate was introduced into reactor with 150 ml of water. The mixture was stirred and heated ($T_j$=85° C.), to 75° C., dissolution of most of the solid was observed. The resulting slurry was stirred at 75° C. for 90 minutes and then cooled to 25° C. 100 ml of IPA was added and the batch was cooled to 5° C. After stirring for 30 min at 5° C. the batch was filtered, the solid washed with 30 ml IPA and dried under vacuum at 50° C. to constant mass.
  Wet solid—50.2 g
  Dry solid—37.7 g
  Yield—93.2% (calculated according to starting material L.O.D.=20%)
Analysis:
Solid:
  Appearance—White solid
  S-isomer—0.10% area
  IDD—no additional peaks detected
  1-Aminoindan—N.D.

Example 52

Slurry-to-Slurry Re-Crystallization from 4 Volumes of Water and Isopropanol, $T_j$=85° C., Prolonged Cooling Time 50.0 g of Rasagiline Tartrate was introduced into reactor with 150 ml of water. The mixture was stirred and heated ($T_j$=85° C.), to 75° C., dissolution of most of the solid was observed. The resulting slurry was stirred at 75° C. for 90 minutes and then cooled to 25° C. 40 ml of IPA was added and the batch was cooled to 2° C. After stirring for 12 hours at 1-2° C. the batch was filtered, the solid washed with 30 ml IPA and dried under vacuum at 50° C. to constant mass.
  Wet solid—52.5 g
  Dry solid—38.1 g
  Yield—95.2% (calculated according to starting material L.O.D.=20%)
Analysis:
Solid:
  Appearance—white solid
  S-isomer—0.05% area
  IDD—no additional peaks detected
  1-Aminoindan—N.D.

The results of parameterization experiments are summarized below in Table 5. The data show that re-crystallization process parameter as processing time and temperature have strong effect on Tartrate optical purification.

TABLE 5.1

Effect of process parameters on Rasagiline Tartrate purification

| Example No. | Re-crystallization temperature, ° C. $T_j$ | $T_r$ | Time min | Cooling Time, hrs | Yield % | S-isomer % | IDD, (AI) (%) |
|---|---|---|---|---|---|---|---|
| 47 | 100 | 90 | 90 | 0.5 | 93.7 | 0.01 | N.D. |
| 48 | 65 | 63 | 90 | 0.5 | 94.5 | 0.32 | L.T. 0.08 |
| 49 | 85 | 75 | 15 | 0.5 | 93.7 | 0.19 | N.D. |
| 50 | 85 | 75 | 150 | 0.5 | 96.0 | 0.10 | N.D. |
| 51 | 85 | 75 | 90 | 0.5 | 93.2 | 0.10 | N.D. |
| 52 | 85 | 75 | 90 | 12 | 95.2 | 0.05 | N.D. |

Decrease of re-crystallization temperature from 75° C. to 63° C. and re-crystallization time from 90 to 15 minutes causes significant increase of S-isomer level in the solid product. At the same time no significant effect of the process parameters on the Yield was observed.

Figure 4:
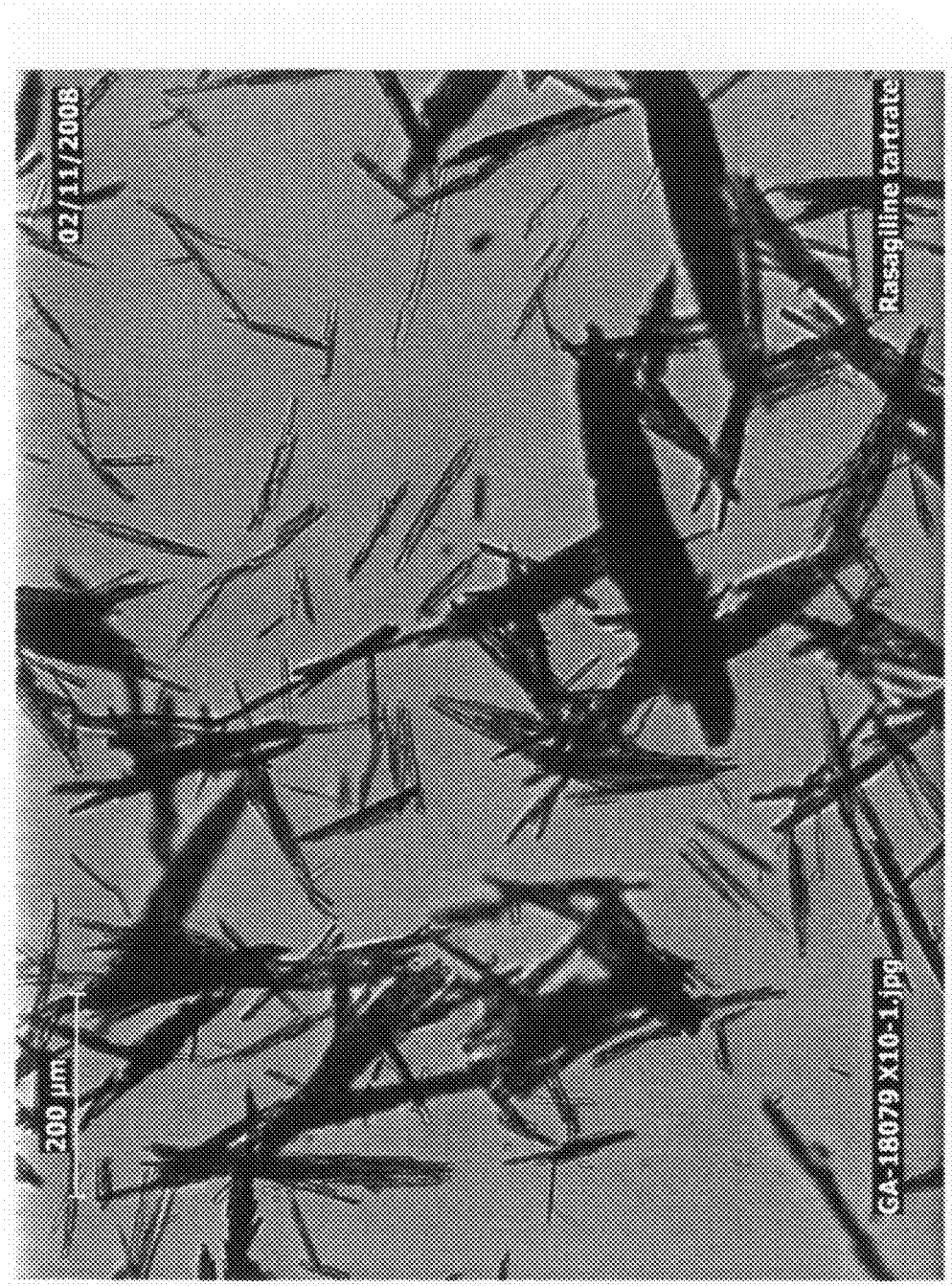
FIG. 4 shows the particle size and shapes of the Rasagiline Tartrate before purification.

FIG. 4 shows that during the re-crystallization of the Tartrate salt significant change in the solid morphology take place. Rasagiline Tartrate crystallized from isopropanol or any other organic solvent has needle-like crystal habit.

Figure 5:
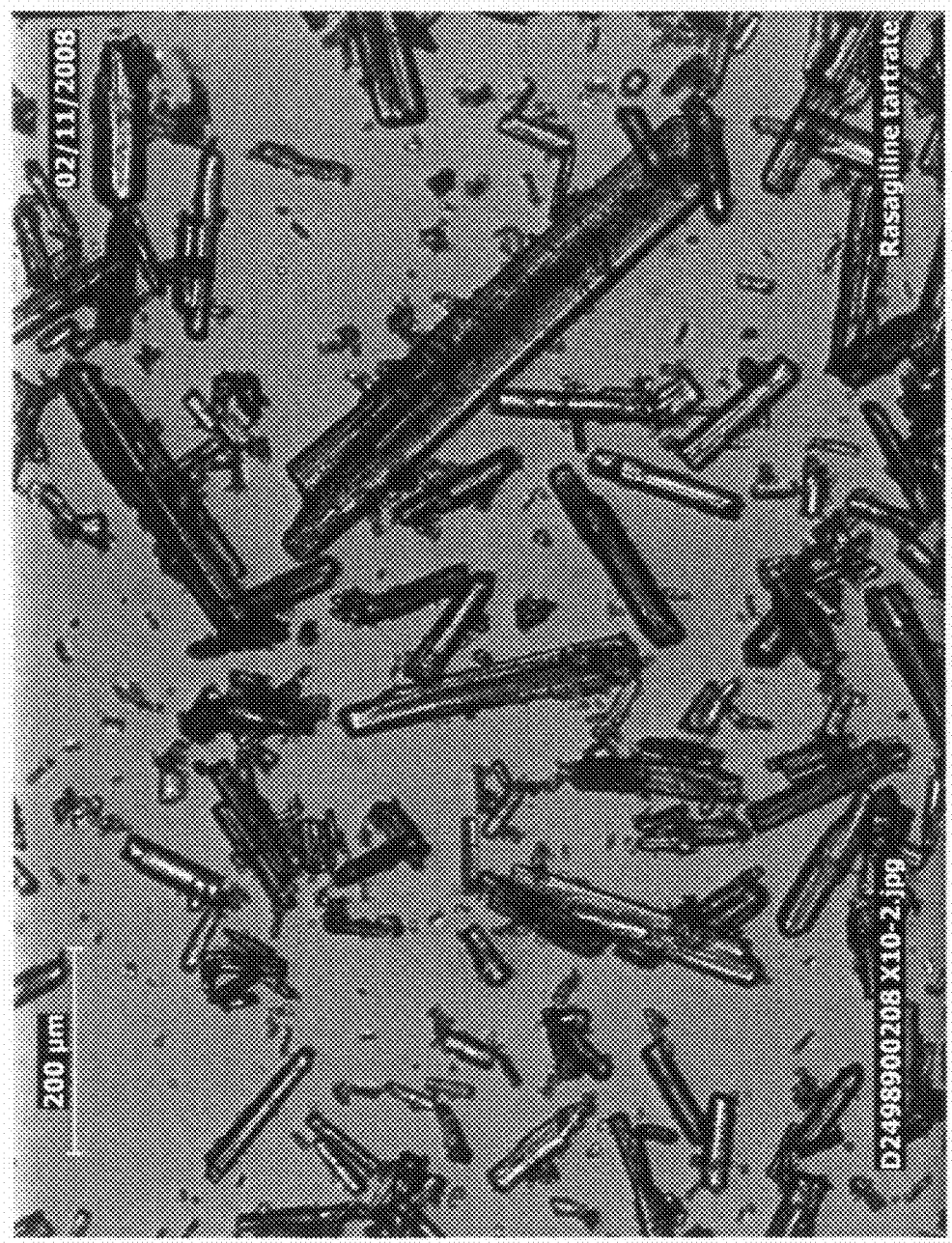
FIG. 5 shows the particle size and shapes of the Rasagiline Tartrate after purification.

As shown in FIGS. 4 and 5, the needle-like crystals of starting Rasagiline Tartrate are transformed to rod-shaped crystals of re-crystallized product.

3.3. Purification of Rasagiline Tartrate on Large Scale

Two batches of purified Rasagiline Tartrate were produced on large scale according to the procedures described in Section 3.2. The process was based on the Example 46.

The results of the production are summarized in Tables 6.1 and 7.1 below.

TABLE 6.1

Large Scale production of Rasagiline Tartrate Pure, Process parameters

| Process parameters: | | Batch 1 | Batch 2 |
|---|---|---|---|
| Starting Rasagiline | | | |
| Tartrate Wet | Kg | 10.0 | 10.0 |
| Dry | kg | 6.97 | 6.97 |
| Stirrer speed | rpm | 240 | 240 |
| Re-crystallization temperature: | | | |
| Start | ° C. | 75 | 75 |
| End | ° C. | 80 | 80 |
| Re-crystallization time | min | 93 | 90 |
| Cooling to 30° C. time | min | 116 | 121 |
| Cooling to 10° C. time | min | 137 | 141 |
| Drying temperature (Bath) | ° C. | 55 | 55 |
| Drying pressure: | | | |
| Start | mm Hg | 49 | 49 |
| End | | 23 | 22 |
| Drying duration | hrs | 15.3 | 15 |
| Dry product yield | Kg % | 6.1 87.5 | 6.0 86.0 |

TABLE 7.1

Quality of large batches of Rasagiline Tartrate Pure

| Test | Specification | Batch 1 | Batch 2 |
|---|---|---|---|
| Description (SI-2000) | White solid | White solid | White solid |
| Enantiomeric purity (limit test by HPLC) | S-isomer; NMT 0.3% | LT 0.3% | LT 0.3% |
| Identification (by HPLC) | RT of the main peak | Conforms | Conforms |
| Chromatographic purity (by HPLC) | AI - NMT 1.5%; Any other - NMT 0.1% | LT 0.08% (QL) L.T. 0.02 | LT 0.08% (QL) L.T. 0.02 |
| L.O.D. | NMT 0.5% | 0.04% | 0.04% |

4. Reprocessing of Rasagiline Base in Large Scale

The batch of Rasagiline base produced in Example 38 was reprocessed in order to reduce the level of S-isomer from 0.35% and to fit the specifications.

The reprocessing procedure was based on re-crystallization Example 42. High yield and good product quality were achieved. Process parameters of the laboratory scale and pilot reprocessing batches are compared in Table 8.1. Product quality of the laboratory and pilot batches is presented in Table 9.1.

The data show that there is no significant effect of the process scale on the reprocessing results. The batch was released by QC/QA and used for stability tests and formulation development.

TABLE 8.1

Rasagiline base re-crystallization parameters on small scale and large scale batches

| | | Small scale | Large scale |
|---|---|---|---|
| Scale, Batch size, starting material | kg | 0.0495 | 3.43 |
| Solvent ratio Ethanol:base | ml/g | 1.33 | 1.35 |
| Water:base | ml/g | 2.57 | 2.60 |
| Percent of water introduced prior to seeding | % | 18.9 | 19.0 |
| Seeding temperature | °C | 12 | 12 |
| Cooling temperature | °C | 2-4 | 3-4 |
| Cooling time | min | 45 | 30 |
| Drying conditions Dryer | | Glass tray in vacuum oven | Hastelloy agitated filter-dryer |
| Temperature | °C | Ambient | 35 |
| Pressure | mbar | 20 | 20-33 |
| Duration | hrs | 16 | 14.6 |
| Yield of dry product | Kg | 0.0455 | 3.05 |
| | % | 91.9 | 89.0 |

TABLE 9.1

Major quality parameters of small scale and large scale batches of re-crystallized Rasagiline base

| | | Small scale | Large scale |
|---|---|---|---|
| Color | | Off-white | Off-white |
| Enantiomeric purity (S-isomer) | % | N.D. | Passes (N.D.) |
| Assay by HPLC | % | 99.8 | 99.7 |
| IDD by HPLC: | % | | |
| 1-Aminoindan | | L.T. 0.05 (Q.L.) | L.T. 0.02 (D.L.) |

TABLE 9.1-continued

Major quality parameters of small scale and large scale batches of re-crystallized Rasagiline base

| | | Small scale | Large scale |
|---|---|---|---|
| 1-Indanone | | L.T. 0.05 (Q.L.) | L.T. 0.02 (D.L.) |
| 3-PAIO | | L.T. 0.05 (Q.L.) | L.T. 0.02 (D.L.) |
| Any other impurity | | N.D. | L.T. 0.02 (D.L.) |
| Melting range | °C | 39.1-39.8 | 39.2-40.6 |

5. Production of Rasagiline Base from Purified Rasagiline Tartrate

Two large scale batches of Rasagiline base were produced with purified Rasagiline Tartrate. In addition, Rasagiline base was held in ethanol solution prior to crystallization during the process.

Process parameters and conditions are summarized below in Tables 10.1, 10.2, and 10.3 in step-by-step order. The data presented in Tables 10.1-10.3 demonstrate good process reproducibility in large scale and salability of the production procedure.

TABLE 10.1

Process parameters or Rasagiline base production, Large scale
Tartrate splitting and Rasagiline base isolation Steps

| Process parameters: | | | Batch 1 | Batch 2 |
|---|---|---|---|---|
| Amount of Rasagiline Tartrate Pure (starting material) | | kg | 6.1 | 6.0 |
| Total amount of 25% NaOH solution | | kg | 5.8 | 5.8 |
| pH after basification | | | 13 | 13 |
| Reactor temperature during the basification and splitting | | °C | 43-49 | 40-50 |
| Duration of the basification and splitting | | hrs | 4 | 4 |
| Toluene evaporation | Duration | hrs | 2.3 | 2.1 |
| | Temperature | °C | 22-60 | 22-60 |
| | Pressure | mmHg | 67-43 | 70-43 |
| Ethanol evaporation | Duration | hrs | 1.5 | 1.3 |
| | Temperature | °C | 21-60 | 19-60 |
| | Pressure | mmHg | 49 | 45-46 |
| Rasagiline base oil dissolution | Duration | min | 32 | 30 |
| | Temperature | °C | 38 | 39 |
| Filtration (0.2µ) and wash | Duration | min | 7 | 5 |
| | Temperature | °C | 38 | 39 |

TABLE 10.2

Process parameters or Rasagiline base production, Large scale
Rasagiline base crystallization Steps

| Process parameters: | | | Batch 1 | Batch 2 |
|---|---|---|---|---|
| Ethanolic solution holding | Duration | hrs | 11.6 | 12.8 |
| | Temperature | °C | 10-2 | 10-17* |
| Amount of water introduced prior to seeding | | kg | 2.0 | 2.0 |
| | | % | 19 | 19 |
| Seeding and breeding | Temperature | °C | 11-12 | 11-12 |
| | Stirrer speed | rpm | 153 | 180 |
| | Duration | min | 116 | 67 |

TABLE 10.2-continued

Process parameters or Rasagiline base
production, Large scale
Rasagiline base crystallization Steps

| Process parameters: | | | Batch 1 | Batch 2 |
|---|---|---|---|---|
| Water addition | Temperature | °C. | 11-14 | 12 |
| | Duration | min | 77 | 60 |
| Cooling | End temperature | °C. | 6 | 6 |
| | Stirrer speed | rpm | 185 | 178 |
| | Duration | min | 120 | 78 |
| Batch stirring prior to filtration | Duration | min | 98 | 60 |
| | Temperature | °C. | 6 | 5 |

*Cooling system failure during the overnight holding of the batch

TABLE 10.3

Process parameters or Rasagiline base
production, Large scale
Solid Rasagiline base isolation - filtration, washing,
drying Steps

| Process parameters: | | | Batch 1 | Batch 2 |
|---|---|---|---|---|
| Filtration and cake purging time | | min | 6 | 15 |
| Washing time (two washes) | | min | 15 | 17 |
| Drying | Pressure | mmHg | 37-22 | 41-22 |
| | Temperature ($T_j$) | °C. | 35 | 35 |
| | Agitator speed | rpm | 7 | 15 |
| | Duration | hrs | 20.2 | 22 |
| Water in dry product by K.F. | | % | 0.07 | 0.06 |
| Dry product yield | | kg | 3.6 | 3.7 |
| | | % | 85.0 | 88.7 |

Quality data for batches of Rasagiline base produced are summarized in Tables 11.1 and 11.2 below.

The data show high purity of the Rasagiline base and reproducibility of its physical properties on pilot scale.

TABLE 11.1

Rasagiline base DS quality

| | | Batch No. | | |
|---|---|---|---|---|
| Test | | 1 | 2 | 3 |
| Description | | Off-white powder | Yellowish solid | Off-white solid |
| Melting range by USP | °C. | 39.2-40.6 | 39.4-40.5 | 39.7-40.6 |
| Water content by coulometric K.F. | % | 0.08 | 0.07 | 0.03 |
| Residue on ignition by USP | % | 0.03 | 0.00 | 0.01 |
| Heavy metals by USP | % | L.T. 0.002 | L.T. 0.002 | L.T. 0.002 |
| Impurities and degradation products by HPLC: | | | | |
| 1-Aminoindan | % | L.T. 0.02 | L.T. 0.02 | L.T. 0.02 |
| 1-Indanone | | L.T. 0.02 | L.T. 0.02 | L.T. 0.02 |
| 3-PAIO | | L.T. 0.02 | L.T. 0.02 | L.T. 0.02 |
| Any other impurity | | L.T. 0.02 | L.T. 0.02 | L.T. 0.02 |
| Total impurities | | L.T. 0.02 | L.T. 0.02 | L.T. 0.02 |
| N-(2-Chloroallyl)-1-aminoindan by LC-MS | ppm | L.T. 1 (passes) | L.T. 1 (passes) | L.T. 1 (passes) |

TABLE 11.1-continued

Rasagiline base DS quality

| | | Batch No. | | |
|---|---|---|---|---|
| Test | | 1 | 2 | 3 |
| Enantiomeric purity (S-isomer by HPLC) | % | L.T. 0.1 | L.T. 0.1 | L.T. 0.1 |
| OVI/Residual Solvents: | ppm | | | |
| Ethanol | | 295 | 205 | L.T. 200 |
| Toluene | | L.T. 200 | 250 | 42 |
| Isopropanol | | L.T. 200 | L.T. 200 | L.T. 200 |
| Assay on dry basis by HPLC | % | 99.7 | 99.9 | 100.2 |

TABLE 11.2

Physical properties of Rasagiline base DS

| | | Batch No. | | |
|---|---|---|---|---|
| Test | | 1 | 2 | 3 |
| Powder density by USP: | g/ml | | | |
| Bulk (BD) | | 0.497 | 0.426 | 0.443 |
| Tapped (TD) | | 0.727 | 0.579 | 0.624 |
| Particle Size Distribution by Malvern: | μm | | | |
| D (0.1) | | 112.5 | 146.3 | 144.7 |
| D (0.5) | | 404.1 | 386.9 | 388.1 |
| D (0.9) | | 1099.4 | 968.6 | 988.6 |
| Morphology by light microscope observation | | Rod shape prime particles Group I | Rod shape prime particles Group I | Rod shape prime particles Group I |

6. Intermediate Products—Time Limitations

There are three new intermediate solid products in the production procedure of Rasagiline base DS:
  Wet Rasagiline Tartrate pure
  Dry Rasagiline Tartrate pure
  Wet Rasagiline base The intermediates should be held for a long period of time between the process operations. A special study was performed in order to prove the stability of the materials under the storage conditions.

6.1. Small Scale Experiments

Example 53

Stability Test for Wet Rasagiline Tartrate Pure

Rasagiline Tartrate Pure wet with isopropanol and water was stored at ambient temperature (RT) in polyethylene bag. The solid was sampled, dried to constant weight and analyzed. The sampling and analysis were performed at time zero, than after 2 weeks and 4 weeks from time zero. The results are presented in Table 12 below.

Example 54

Stability Test for Dried Rasagiline Tartrate Pure

A batch of dry Rasagiline Tartrate Pure produced in Example ?? was stored at ambient temperature (RT) in polyethylene bag. The solid was sampled and analyzed at time zero, than after 2 weeks and 4 weeks from time zero. The results are presented in Table 12.1 below.

Example 55

Stability Test for Wet Rasagiline Base

Rasagiline Base wet with water produced in Example ?? was stored at ambient temperature (RT) in polyethylene bag inside aluminium laminate bag protected from light. The solid was sampled, dried to constant weight under vacuum and analyzed. The sampling and analysis were performed at time zero, than after 2 weeks and 4 weeks from zero time. The results are presented in Table 13.1 below.

TABLE 12.1

Stability tests for wet and dry Rasagiline Tartrate Pure

| Material | Test | | Start (t = 0) | 2 weeks | 4 weeks |
|---|---|---|---|---|---|
| Dry GA-18062 | Description | | White solid | White solid | White solid |
| | S-isomer by HPLC | % | L.T. 0.3 | L.T. 0.3 | L.T. 0.3 |
| | ID by HPLC | | Conforms | Conforms | Conforms |
| | Chromatographic purity by HPLC: | | | | |
| | 1-Aminoindan | % | L.T. 0.03 | L.T. 0.03 | L.T. 0.03 |
| | Any other | % | L.T. 0.03 | L.T. 0.03 | L.T. 0.03 |
| | L.O.D. | % | 0.03 | 0.16 | 0.03 |
| Wet RB-2087 | Description | | White solid | White solid | White solid |
| | S-isomer by HPLC | % | L.T. 0.3 | L.T. 0.3 | L.T. 0.3 |
| | ID by HPLC | | Conforms | Conforms | Conforms |
| | Chromatographic purity by HPLC: | | | | |
| | 1-Aminoindan | % | L.T. 0.03 | L.T. 0.03 | L.T. 0.03 |
| | Any other | % | L.T. 0.03 | L.T. 0.03 | L.T. 0.03 |
| | L.O.D.* | % | 0.01 | 0.05 | 0.04 |

*Samples of wet Rasagiline Tartrate were dried prior to analysis

TABLE 13

Stability test for wet Rasagiline base

| Test | | Start (t = 0) | 2 weeks | 4 weeks |
|---|---|---|---|---|
| Description | | White solid | White solid | White solid |
| Assay by HPLC | % on dry basis | 100.1 | 100.5 | 100.7 |
| IDD by HPLC: | | | | |
| 1-Aminoindan | % | L.T. 0.02 | L.T. 0.02 | L.T. 0.02 |
| 1-Indanone | % | L.T. 0.02 | L.T. 0.02 | L.T. 0.02 |
| 3-PAIO | % | L.T. 0.02 | L.T. 0.02 | L.T. 0.02 |
| Any other | % | L.T. 0.02 | L.T. 0.02 | L.T. 0.02 |
| Total | % | L.T. 0.02 | L.T. 0.02 | L.T. 0.02 |
| ID by HPLC | | Conforms | Conforms | Conforms |
| Water content by CKF | % | 0.04 | 0.04 | 0.03 |
| Enantiomeric purity by HPLC (S-isomer) | % | L.T. 0.1% (Passes) | L.T. 0.1% (Passes) | L.T. 0.1% (Passes) |

6.2. Results and Discussion

The data presented in the Tables 12.1 and 13.1 shows that no changes in purity of all solid intermediates occur during 4 weeks of storage. All products conformed to the specifications after completion of 4-weeks stability test. Time limitations for the production intermediates are presented in Table 14.1.

TABLE 14.1

Rasagiline base intermediate product - time limitations

| No. | Product | Storage temperature, °C. | Time limitation |
|---|---|---|---|
| 1 | Wet Rasagiline Tartrate Pure | R.T. | One month |
| 2 | Dry Rasagiline Tartrate Pure | R.T. | One month |
| 3 | Wet Rasagiline base | +2-+8° C. | One month |

What is claimed is:

1. Crystalline R(+)-N-propargyl-1-aminoindan containing water at an amount of less than 0.5% by weight.

2. The crystalline R(+)-N-propargyl-1-aminoindan of claim 1 containing water at an amount of no more than 0.06% by weight.

3. A pharmaceutical composition comprising the crystalline R(+)-N-propargyl-1-aminoindan of claim 1 and a pharmaceutically acceptable carrier.

4. The pharmaceutical composition of claim 3, formulated for oral administration.

5. The pharmaceutical composition of claim 3, formulated for transdermal application.

6. The pharmaceutical composition of claim 5 in the form of a transdermal patch.

7. A process for drying solid R(+)-N-propargyl-1-aminoindan comprising exposing the solid R(+)-N-propargyl-1-aminoindan to a temperature of less than 40° C. and a pressure of between 2-1013.3 mbar for an amount of time suitable to dry the solid R(+)-N-propargyl-1-aminoindan.

8. A process for preparing a pharmaceutical composition comprising crystalline R(+)-N-propargyl-1-aminoindan containing water at an amount of less than 0.5% by weight and a pharmaceutically acceptable carrier, comprising:
    combining the dried R(+)-N-propargyl-1-aminoindan prepared by the process of claim 7 with the pharmaceutically acceptable carrier, thereby preparing the pharmaceutical composition.

9. The process of claim 7, wherein the temperature for drying is less than 35° C.

10. The process of claim 7, wherein the temperature for drying is less than 25° C.

11. The process of claim 7, wherein the pressure for drying is higher than 20 mbar.

12. The process of claim 7, wherein the amount of time for drying is at least 45 hours.

13. A process for producing a validated batch of a drug product containing crystalline R(+)-N-propargyl-1-aminoindan and at least one pharmaceutically acceptable carrier for distribution comprising:
    a) producing a batch of the drug product;
    b) determining the water content by weight with a sample of the batch; and
    c) validating the batch for distribution only if the crystalline R(+)-N-propargyl-1-aminoindan in the batch contains less than 0.5% water by weight.

14. The process of claim 13, wherein the batch is validated only if the crystalline R(+)-N-propargyl-1-aminoindan in the batch contains less than 0.06% water by weight.

15. A process for producing crystalline R(+)-N-propargyl-1-aminoindan comprising:

i) dissolving the salt of R(+)-N-propargyl-1-aminoindan in water to form a solution;

ii) adding a water-soluble organic solvent to the solution;

iii) cooling the solution to a temperature of about 0-10° C.;

iv) obtaining the salt of R(+)-N-propargyl-1-aminoindan from the suspension;

v) dissolving the salt of R(+)-N-propargyl-1-aminoindan obtained in step iv) in water to form a solution;

vi) cooling solution of step v) to a temperature of 0-15° C.;

vii) basifying cooled solution to a pH of 9.5-12.5 to form a suspension of crystalline R(+)-N-propargyl-1-aminoindan; and viii) separating said crystalline R(+)-N-propargyl-1-aminoindan from the suspension.

16. The process of claim 15, wherein the salt of R(+)-N-propargyl-1-aminoindan obtained in step iv) has a higher optical purity relative to the salt of R(+)-N-propargyl-1-aminoindan in step i).

17. The process of claim 15, wherein the salt of R(+)-N-propargyl-1-aminoindan is a tartrate salt.

* * * * *